(12) United States Patent
Harris et al.

(10) Patent No.: US 7,608,689 B2
(45) Date of Patent: Oct. 27, 2009

(54) METHODS FOR ENHANCING THE DEGRADATION OR CONVERSION OF CELLULOSIC MATERIAL

(75) Inventors: Paul Harris, Carnation, WA (US); Michael Rey, Davis, CA (US); Hanshu Ding, Davis, CA (US)

(73) Assignee: Novozymes, Inc., David, CA (US)

( * ) Notice: Subject to any disclaimer, the term of this patent is extended or adjusted under 35 U.S.C. 154(b) by 0 days.

(21) Appl. No.: 11/541,099

(22) Filed: Sep. 29, 2006

(65) Prior Publication Data

US 2007/0077630 A1 Apr. 5, 2007

Related U.S. Application Data

(60) Provisional application No. 60/722,579, filed on Sep. 30, 2005.

(51) Int. Cl.
*C07K 1/00* (2006.01)
*C12N 9/24* (2006.01)
*C07H 21/04* (2006.01)

(52) U.S. Cl. ........................ 530/350; 435/200; 536/23.2
(58) Field of Classification Search ................. 435/200, 435/41; 536/23.2; 530/350
See application file for complete search history.

(56) References Cited

U.S. PATENT DOCUMENTS 7,271,244 B2 * 9/2007 Dotson et al. ................ 530/350
2003/0113734 A1 6/2003 Dunn-Coleman et al.

FOREIGN PATENT DOCUMENTS

WO WO 03/052055 A2 6/2003

OTHER PUBLICATIONS

Foreman et al. [J. Biol. Chem. 278(34): 31988-319997, Aug. 22, 2003].*

* cited by examiner

*Primary Examiner*—Tekchand Saidha
(74) *Attorney, Agent, or Firm*—Robert L. Starnes

(57) ABSTRACT

The present invention relates to methods for degrading or converting a cellulosic material and for producing a substance from a cellulosic material.

13 Claims, 5 Drawing Sheets

```
GGATCTAAGCCCCATGCTGATATGAAGTCCTGCGCCATTCTTGCAGCCCTTGGCTGTCTTGCCGGGAGCGTTCTCGGCCATG
            M  K  S  C  A  I  L  A  A  L  G  C  L  A  G  S  V  L  G  H
GACAAGTCCAAAACTTCACGATCAATGGACAATACAATCAGGGTTTCATTCTGATTACTATCAGAAGCAGAATACT
 G  Q  V  Q  N  F  T  I  N  G  Q  Y  N  Q  G  F  I  L  D  Y  Y  Q  K  Q  N  T
GGTCACTTCCCCAACGTTGCTGGCTGTACGCCGAGGACCTGGACCTAGACCTTCATCTCCCCTGACCATACACCACGCC
 G  H  F  P  N  V  A  G  W  Y  A  E  D  L  D  L  G  F  I  S  P  D  Q  Y  T  T  P
CGACATTGTCTGCCACAAGAACGGGCCCCAGGTGCCATTTCTGCCACTGCAGCAACATGTCTTCCAAT
 D  I  V  C  H  K  N  A  P  G  A  I  S  A  T  A  A  A  G  S  N  I  V  F  Q
GGGGCCCTGGCGTCTGGCCTCACCCCTACGGTCCCATCGTTACCTAGTGGCTGAGTGCAGCGGATCGTGCACGACCGTG
 G  P  L  A  S  G  L  T  P  T  V  P  I  V  T  *  V  V  E  C  S  G  S  C  T  T  V
TGGCCCGTGGGTGTGGCTGGGTCAAGATTCAGGAGGCCATCAAGTCTGGGCGCAGCAGGATCT
 W  G  P  G  V  W  P  H  P  Y  G  P  I  V  T  Y  V  V  E  C  S  G  S  C  T  T  V
AACAAGAACAACCTGCGCTGGGTCAAGATTCAGGAGGCCATCAAGTCTGGGCGCAGCAGGATCT
 N  K  N  N  L  R  W  V  K  I  Q  E  A  G  I  N  Y  N  T  Q  V  W  A  Q  Q  D  L
GATCAACCAGGGCAACAAGTGGACTGTGAAGATCCCGTCGAGCCTGAGAACTATGTCTTCCGCCATGAACTTC
 I  N  Q  G  N  K  W  T  V  K  I  P  S  S  L  R  P  G  N  Y  V  F  R  H  E  L
TTGCTGCCCATGGTGCCTCTAGTGCGAACGGCATGCAGAACTATCTCAGTGCGTGAACATCGCCGTCACAGGCTGGGC
 L  A  A  H  G  A  S  A  N  G  M  Q  N  Y  P  Q  C  V  N  I  A  V  T  G  S  G
ACGAAAGCGCTCCCTGCCGGAACTCCTGCAACTCAGCTCGAACAAGCCCAGCCATCTTGTTCAACCCTTACAC
 T  K  A  L  P  A  G  T  P  A  T  Q  L  Y  K  P  T  D  P  G  I  L  F  N  P  Y  T
AACAATCACGAGACTACACCATCCCTGCCAAGGCTAGATCCAGGGGTACGGTGTTGGCGTTCGTGAAG
 T  I  T  S  Y  T  I  P  G  P  A  L  W  Q  G
TCGGAGCTGTTGACAAGGATATCTGATGATGAACGGAGAGGACTGATGGGCGTGACTGAGTGTATATATTTTGATGACC
AAATTGTATACGAAATCCGAACGCATGTGATCATTGTTTATCCCTGTAGTATATTGTCTCCAGGCTGCTAAGAGCCCAC
CGGGTGTATTACGGCAACAAAGTCAGGAATTTGGGTGGCAATGAACGCAGGTCTCCATGAATGTATATGTGAAGAGGCAT
CGGCTGGCATGGGCATTACCAGATATAGGCCCTGTGAAACATATAGTACTTGAACGTGCTACTGAACGGATCATAAGCA
AGTCATCAACATGTGAAAAAAACACTACACATGTAAAAAAAAAAAAAAAAAA
```

METHODS FOR ENHANCING THE DEGRADATION OR CONVERSION OF CELLULOSIC MATERIAL

CROSS-REFERENCE TO RELATED APPLICATION

This application claims the benefit of U.S. Provisional Application No. 60/722,529, filed Sep. 30, 2005, which application is incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

BACKGROUND OF THE INVENTION

1. Field of the Invention

The present invention relates to methods for degrading or converting a cellulosic material and for producing a substance from a cellulosic material.

2. Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

It would be advantageous in the art to improve the ability to convert cellulosic feedstocks.

U.S. Published Patent Application Ser. No. 2003/0113734 discloses an isolated cellulase protein, identified as EGVII, and nucleic acids which encode EGVII.

It is an object of the present invention to provide isolated polypeptides having cellulolytic enhancing activity and isolated nucleic acid sequences encoding the polypeptides to improve the conversion of cellulosic feedstocks.

SUMMARY OF THE INVENTION

The present invention relates to methods for degrading or converting a cellulosic material, comprising: treating the cellulosic material with an effective amount of one or more cellulolytic proteins in the presence of an effective amount of a polypeptide having cellulolytic enhancing activity, wherein the presence of the polypeptide having cellulolytic enhancing activity increases the degradation of cellulosic material compared to the absence of the polypeptide having cellulolytic enhancing activity and wherein the polypeptide having cellulolytic enhancing activity is selected from the group consisting of:

(a) a polypeptide comprising [ILMV]-P-x(4,5)-G-x-Y-[ILMV]-x-R-x-[EQ]-x(3)-A-[HNQ], wherein x is any amino acid, x(4,5) is any amino acid at 4 or 5 contiguous positions, and x(3) is any amino acid at 3 contiguous positions;

(b) a polypeptide comprising an amino acid sequence which has at least 70% identity with the mature polypeptide of SEQ ID NO: 2;

(c) a polypeptide encoded by a polynucleotide which hybridizes under at least medium stringency conditions with (i) the mature polypeptide coding sequence of SEQ ID NO: 1, (ii) the genomic DNA sequence comprising the mature polypeptide coding sequence of SEQ ID NO: 1, or (iii) a complementary strand of (i) or (ii); and (d) a variant comprising a conservative substitution, deletion, and/or insertion of one or more amino acids of the mature polypeptide of SEQ ID NO: 2.

The present invention also relates to methods for producing a substance, comprising:

(A) saccharifying a cellulosic material with an effective amount of one or more cellulolytic proteins in the presence of an effective amount of a polypeptide having cellulolytic enhancing activity, wherein the presence of the polypeptide having cellulolytic enhancing activity increases the degradation of cellulosic material compared to the absence of the polypeptide having cellulolytic enhancing activity and wherein the polypeptide having cellulolytic enhancing activity is selected from the group consisting of:

(i) a polypeptide comprising [ILMV]-P-x(4,5)-G-x-Y-[ILMV]-x-R-x-[EQ]-x(3)-A-[HNQ], wherein x is any amino acid, x(4,5) is any amino acid at 4 or 5 contiguous positions, and x(3) is any amino acid at 3 contiguous positions; and (ii) a polypeptide comprising an amino acid sequence which has at least 70% identity with the mature polypeptide of SEQ ID NO: 2;

(iii) a polypeptide encoded by a polynucleotide which hybridizes under at least medium stringency conditions with (a) the mature polypeptide coding sequence of SEQ ID NO: 1, (b) the genomic DNA sequence comprising the mature polypeptide coding sequence of SEQ ID NO: 1, or (c) a complementary strand of (i) or (ii); and (iv) a variant comprising a conservative substitution, deletion, and/or insertion of one or more amino acids of the mature polypeptide of SEQ ID NO: 2;

(B) fermenting the saccharified cellulosic material of step (a) with one or more fermenting microorganisms; and (C) recovering the substance from the fermentation.

In a preferred aspect, the mature polypeptide is amino acids 20 to 249 of SEQ ID NO: 2. In another preferred aspect, the mature polypeptide coding sequence is nucleotides 77 to 766 of SEQ ID NO: 1.

The present invention further relates to detergent compositions comprising such polypeptides having cellulolytic enhancing activity.

BRIEF DESCRIPTION OF THE FIGURES

FIG. 1 shows the cDNA sequence and the deduced amino acid sequence of a *Trichoderma reesei* RutC30 (ATCC 56765) GH61B polypeptide having cellulolytic enhancing activity (SEQ ID NOs: 1 and 2, respectively). Predicted introns are italicized. The predicted signal peptide is underlined.

DEFINITIONS

Figure 2:
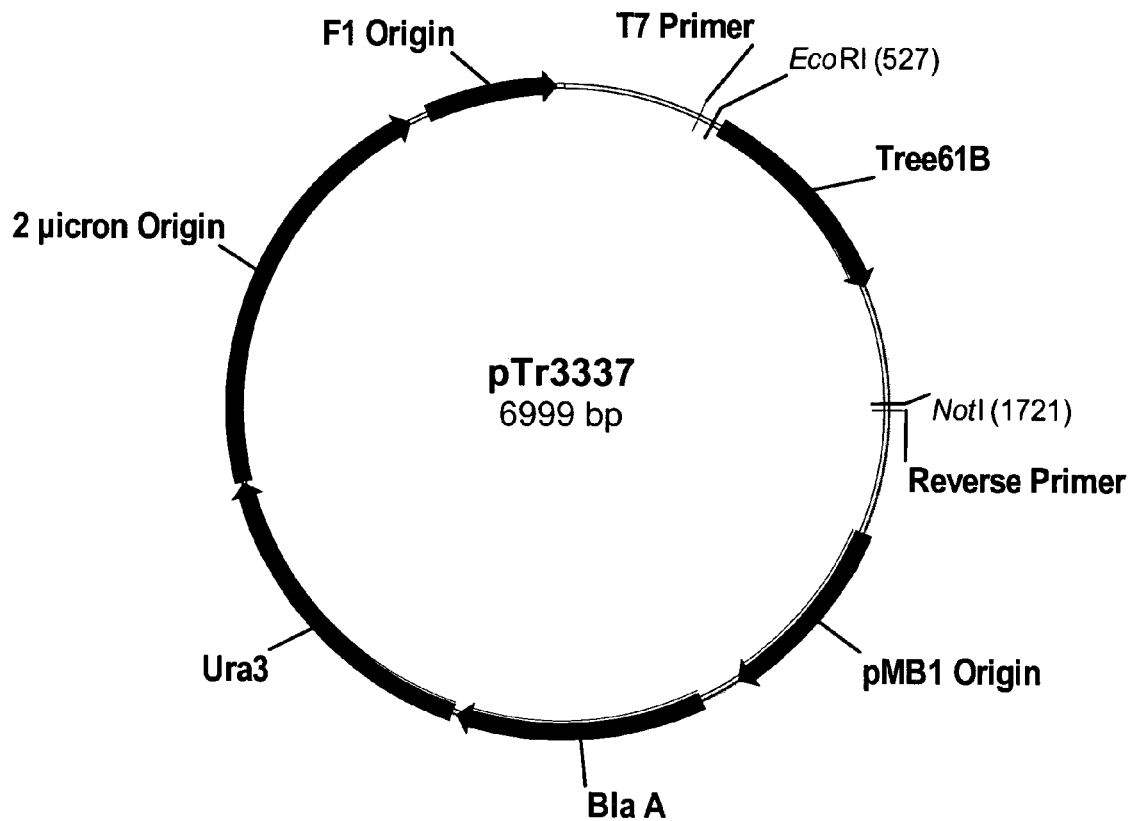
FIG. 2 shows a restriction map of pTr3337.

Cellulolytic enhancing activity: The term "cellulolytic enhancing activity" is defined herein as a biological activity which enhances the hydrolysis of a cellulosic material by proteins having cellulolytic activity. For purposes of the present invention, cellulolytic enhancing activity is determined by measuring the increase in reducing sugars from the hydrolysis of a cellulosic material by cellulolytic protein under the following conditions: 5.0 mg of cellulolytic protein/g of cellulose in PCS for 5-7 day at 50° C. in the presence and absence of 0.01-2.5 mg of cellulolytic enhancing activity per g of cellulose in PCS compared to a control hydrolysis with equal total protein loading without cellulolytic enhancing activity (5.01-7.5 mg of cellulolytic protein/g of cellulose in PCS). In a preferred aspect, a mixture of Celluclast® 1.5 L (Novozymes A/S, Bagsværd, Denmark) in the presence of 3% *Aspergillus oryzae* beta-glucosidase (recombinantly produced in *Aspergillus oryzae* according to WO 02/095014) or 3% *Aspergillus fumigatus* beta-glucosidase (recombinantly produced in *Aspergillus oryzae* according to Example 22 of WO 02/095014) of cellulase protein loading is used as the source of the cellulolytic activity.

The polypeptides having cellulolytic enhancing activity have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the cellulolytic enhancing activity of the polypeptide of the mature polypeptide of SEQ ID NO: 2.

Cellulolytic activity: The term "cellulolytic activity" is defined herein as a biological activity which hydrolyzes a cellulosic material. For purposes of the present invention, cellulolytic activity is determined by measuring the increase in hydrolysis of a cellulosic material by a cellulolytic mixture under the following conditions: 1-10 mg of cellulolytic protein/g of cellulose in PCS for 5-7 day at 50° C. compared to a control hydrolysis without addition of cellulolytic protein. In a preferred aspect, a mixture of Celluclast® 1.5 L (Novozymes A/S, Bagsværd, Denmark) in the presence of 3% *Aspergillus oryzae* beta-glucosidase (recombinantly produced in *Aspergillus oryzae* according to WO 02/095014) or 3% *Aspergillus fumigatus* beta glucosidase (recombinantly produced in *Aspergillus oryzae* according to Example 22 of WO 02/095014) of cellulase protein loading as the source of the cellulolytic activity.

Pre-treated corn stover: The term "PCS" or "Pre-treated Corn Stover" is defined herein as a cellulosic material derived from corn stover by treatment with heat and dilute acid. For purposes of the present invention, PCS is made by the method described in Example 1, or variations thereof in time, temperature and amount of acid.

Family 61 glycoside hydrolase: The term "Family 61 glycoside hydrolase" or "Family GH61" is defined herein as a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. Presently, Henrissat lists the GH61 Family as unclassified indicating that properties such as mechanism, catalytic nucleophile/base, catalytic proton donors, and 3-D structure are not known for polypeptides belonging to this family.

Cellulosic material: The cellulosic material can be any material containing cellulose. Cellulose is generally found, for example, in the stems, leaves, hulls, husks, and cobs of plants or leaves, branches, and wood of trees. The cellulosic material can also be, but is not limited to, herbaceous material, agricultural residues, forestry residues, municipal solid wastes, waste paper, and pulp and paper mill residues. It is understood herein that the cellulose may be in the form of lignocellulose, a plant cell wall material containing lignin, cellulose, and hemicellulose in a mixed matrix.

In a preferred aspect, the cellulosic material is corn stover. In another preferred aspect, the cellulosic material is corn fiber. In another preferred aspect, the cellulosic material is rice straw. In another preferred aspect, the cellulosic material is paper and pulp processing waste. In another preferred aspect, the cellulosic material is woody or herbaceous plants. In another preferred aspect, the cellulosic material is bagasse.

The cellulosic material may be used as is or may be subjected to pretreatment, using conventional methods known in the art. For example, physical pretreatment techniques can include various types of milling, irradiation, steaming/steam explosion, and hydrothermolysis; chemical pretreatment techniques can include dilute acid, alkaline, organic solvent, ammonia, sulfur dioxide, carbon dioxide, and pH-controlled hydrothermolysis; and biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, DC, 179-212; Ghosh, P., and Singh, A., 1993, Physicochemical and biological treatments for enzymatic/microbial conversion of lignocellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, DC, chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson, L., and Hahn-Hagerdal, B., 1996, Fermentation of lignocellulosic hydrolysates for ethanol production, *Enz. Microb. Tech.* 18: 312-331; and Vallander, L., and Eriksson, K.-E. L., 1990, Production of ethanol from lignocellulosic materials: State of the art, *Adv. Biochem. Eng./Biotechnol.* 42: 63-95).

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides having cellulolytic enhancing activity are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Mature polypeptide: The term "mature polypeptide" is defined herein as a polypeptide having cellulolytic enhancing activity that is in its final form following translation and any post-translational modifications, such as N-terminal processing, C-terminal truncation, glycosylation, phosphorylation, etc.

Mature polypeptide coding sequence: The term "mature polypeptide coding sequence" is defined herein as a nucleotide sequence that encodes a mature polypeptide having cellulolytic enhancing activity.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The output of Needle labeled "longest identity" is used as the percent identity and is calculated as follows:

(Identical Residues×100)/(Length of Alignment−
Number of Gaps in Alignment)

For purposes of the present invention, the degree of identity between two nucleotide sequences is determined using the Needleman-Wunsch algorithm (Needleman and Wunsch, 1970, *J. Mol. Biol.* 48: 443453) as implemented in the Needle program of EMBOSS with gap open penalty of 10, gap extension penalty of 0.5, and the EDNAFULL matrix. The output of Needle labeled "longest identity" is used as the percent identity and is calculated as follows:

(Identical Residues×100)/(Length of Alignment−
Number of Gaps in Alignment)

Homologous sequence: The term "homologous sequence" is defined herein as sequences with an E value (or expectancy score) of less than 0.001 using the blastp (for protein databases) or tblastn (for nucleic acid databases) algorithms with the BLOSUM62 matrix, wordsize 3, gap existence cost 11, gap extension cost 1, no low complexity filtration, and the mature GH61B protein sequence as query". See Altschul et al., 1997, *Nucleic Acids Res.* 25: 3389-3402.

Polypeptide Fragment: The term "polypeptide fragment" is defined herein as a polypeptide having one or more amino acids deleted from the amino and/or carboxyl terminus of the mature polypeptide of SEQ ID NO: 2, or a homologous sequence thereof, wherein the fragment has cellulolytic enhancing activity. Preferably, a fragment of the mature polypeptide of SEQ ID NO: 2 contains at least 200 amino acid residues, more preferably at least 210 amino acid residues, and most preferably at least 220 amino acid residues.

Subsequence: The term "subsequence" is defined herein as a nucleotide sequence having one or more nucleotides deleted from the 5' and/or 3' end of the mature polypeptide coding sequence of SEQ ID NO: 1, or a homologous sequence thereof, wherein the subsequence encodes a polypeptide fragment having cellulolytic enhancing activity. Preferably, a subsequence of the mature polypeptide coding sequence of SEQ ID NO: 1 contains at least 600 nucleotides, more preferably at least 630 nucleotides, and most preferably at least 660 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence.

Control sequence: The term "control sequences" is defined herein to include all components, which are necessary or advantageous for the expression of a polynucleotide encoding a polypeptide. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG and TGA. The coding sequence may be a DNA, cDNA, or recombinant nucleotide sequence.

Expression: The term "expression" includes any step involved in the production of a polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide.

Modification: The term "modification" means herein any chemical modification of the polypeptide consisting of the mature polypeptide of SEQ ID NO: 2 or a homologous sequence thereof; as well as genetic manipulation of the DNA encoding such a polypeptide. The modification can be substitutions, deletions and/or insertions of one or more amino acids as well as replacements of one or more amino acid side chains.

Artificial variant: When used herein, the term "artificial variant" means a polypeptide having cellulolytic enhancing activity produced by an organism expressing a modified nucleotide sequence of the mature polypeptide coding sequence of SEQ ID NO: 1 or a homologous sequence thereof. The modified nucleotide sequence is obtained through human intervention by modification of the nucleotide sequence disclosed in SEQ ID NO: 1 or a homologous sequence thereof.

DETAILED DESCRIPTION OF THE INVENTION

The present invention relates to methods for degrading or converting a cellulosic material, comprising: treating the cellulosic material with an effective amount of a cellulolytic protein in the presence of an effective amount of the polypeptide having cellulolytic enhancing activity, wherein the presence of the polypeptide having cellulolytic enhancing activity increases the degradation of cellulosic material compared to the absence of the polypeptide having cellulolytic enhancing activity and wherein the polypeptide having cellulolytic enhancing activity is selected from the group consisting of:

(a) a polypeptide comprising [ILMV]-P-x(4,5)-G-x-Y-[ILMV]-x-R-x-[EQ]-x(3)-A-[HNQ], wherein x is any amino acid, x(4,5), is any amino acid at 4 or 5 contiguous positions, and x(3) is any amino acid at 3 contiguous positions;

(b) a polypeptide comprising an amino acid sequence which has at least 70% identity with the mature polypeptide of SEQ ID NO: 2;

(c) a polypeptide encoded by a polynucleotide which hybridizes under at least medium stringency conditions with (i) the mature polypeptide coding sequence of SEQ ID NO: 1, (ii) the genomic DNA sequence comprising the mature polypeptide coding sequence of SEQ ID NO: 1, or (iii) a complementary strand of (i) or (ii); and (d) a variant comprising a conservative substitution, deletion, and/or insertion of one or more amino acids of the mature polypeptide of SEQ ID NO: 2.

The present invention further comprises recovering the degraded or converted cellulosic material. Soluble products of degradation or conversion of the cellulosic material can be separated from the insoluble cellulosic material using technology well known in the art such as centrifugation, filtration, and gravity settling.

The present invention also relates to methods for producing a substance, comprising: (A) saccharifying a cellulosic material with an effective amount of one or more cellulolytic proteins in the presence of an effective amount of the polypeptide having cellulolytic enhancing activity, wherein the presence of the polypeptide having cellulolytic enhancing activity increases the degradation of cellulosic material compared to the absence of the polypeptide having cellulolytic enhancing activity and wherein the polypeptide having cellulolytic enhancing activity is selected from the group consisting of: (i) a polypeptide comprising [ILMV]-P-x(4,5)-G-x-Y-[ILMV]-x-R-x-[EQ]-x(3)-A-[HNQ], wherein x is any amino acid, x(4,5) is any amino acid at 4 or 5 contiguous positions, and x(3) is any amino acid at 3 contiguous positions; (ii) a polypeptide comprising an amino acid sequence which has at least 70% identity with the mature polypeptide of SEQ ID NO: 2; (iii) a polypeptide encoded by a polynucleotide which hybridizes under at least medium stringency conditions with (a) the mature polypeptide coding sequence of SEQ ID NO: 1, (b) the genomic DNA sequence comprising the mature polypeptide coding sequence of SEQ ID NO: 1, or (c) a complementary strand of (a) or (b); and (iv) a variant comprising a conservative substitution, deletion, and/or insertion of one or more amino acids of the mature polypeptide of SEQ ID NO: 2; (B) fermenting the saccharified cellulosic material of step (a) with one or more fermenting microorganisms; and (C) recovering the substance from the fermentation.

The polypeptides having cellulolytic enhancing activity and host cells described herein may be used in the production of monosaccharides, disaccharides, and polysaccharides as chemical or fermentation feedstocks from biomass for the production of ethanol, plastics, other products or intermediates. In particular, the polypeptides and host cells may be used to increase the value of processing residues (dried distillers grain, spent grains from brewing, sugarcane bagasse, etc.) by partial or complete solubilization of cellulose or hemicellulose. In boosting the processing by cellulolytic proteins of cellulosic material to glucose, xylose, mannose, galactose, and arabinose, their polymers, or products derived from them as described below, the polypeptides having cellulolytic enhancing activity may be in the form of a crude fermentation broth with or without the cells or in the form of a semi-purified or purified enzyme preparation. The cellulolytic enhancing protein may be a monocomponent preparation, e.g., a Family 61 protein, a multicomponent protein preparation, e.g., a number of Family 61 proteins, or a combination of multicomponent and monocomponent protein preparations. The cellulolytic enhancing proteins may boost the activity of cellulolytic proteins, either in the acid, neutral, or alkaline pH-range. Alternatively, a host cell may be used as a source of such a polypeptide in a fermentation process with the biomass. The host cell may also contain native or heterologous genes that encode cellulolytic protein as well as other enzymes useful in the processing of biomass.

Biomass can include, but is not limited to, wood resources, municipal solid waste, wastepaper, crops, and crop residues (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York).

The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Polypeptides Having Cellulolytic Enhancing Activity and Polynucleotides Thereof

In a first aspect, the isolated polypeptides having cellulolytic enhancing activity, comprise the following motif:

[ILMV]-P-x(4,5)-G-x-Y-[ILMV]-x-R-x-[EQ]-x(3)-A-[HNQ], wherein x is any amino acid, x(4,5) is any amino acid at 4 or 5 contiguous positions, and x(3) is any amino acid at 3 contiguous positions. In the above motif, the accepted IUPAC single letter amino acid abbreviation is employed.

In a second aspect, the isolated polypeptides having cellulolytic enhancing activity have an amino acid sequence which has a degree of identity to the mature polypeptide of SEQ ID NO: 2 (i.e., the mature polypeptide) of at least 75%, preferably at least 80%, more preferably at least 85%, even more preferably at least 90%, most preferably at least 95%, and even most preferably at least 96%, 97%, 98%, or 99%, which have cellulolytic enhancing activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide having cellulolytic enhancing activity of the present invention preferably comprises the amino acid sequence of SEQ ID NO: 2 or an allelic variant thereof; or a fragment thereof that has cellulolytic enhancing activity. In a preferred aspect, a polypeptide comprises the amino acid sequence of SEQ ID NO: 2. In another preferred aspect, a polypeptide comprises the mature polypeptide of SEQ ID NO: 2. In another preferred aspect, a polypeptide comprises amino acids 20 to 249 of SEQ ID NO: 2, or an allelic variant thereof; or a fragment thereof that has cellulolytic enhancing activity. In another preferred aspect, a polypeptide comprises amino acids 20 to 249 of SEQ ID NO: 2. In another preferred aspect, a polypeptide consists of the amino acid sequence of SEQ ID NO: 2 or an allelic variant thereof; or a fragment thereof that has cellulolytic enhancing activity. In another preferred aspect, a polypeptide consists of the amino acid sequence of SEQ ID NO: 2. In another preferred aspect, a polypeptide consists of the mature polypeptide of SEQ ID NO: 2. In another preferred aspect, a polypeptide consists of amino acids 20 to 249 of SEQ ID NO: 2 or an allelic variant thereof; or a fragment thereof that has cellulolytic enhancing activity. In another preferred aspect, a polypeptide consists of amino acids 20 to 249 of SEQ ID NO: 2.

In a third aspect, the present invention relates to isolated polypeptides having cellulolytic enhancing activity which are encoded by polynucleotides which hybridize under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 1, (ii) the genomic DNA sequence comprising the mature polypeptide coding sequence of SEQ ID NO: 1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). A subsequence of the mature polypeptide coding sequence of SEQ ID NO: 1 contains at least 100 contiguous nucleotides or preferably at least 200 contiguous nucleotides. Moreover, the subsequence may encode a polypeptide fragment which has cellulolytic enhancing activity. In a preferred aspect, the mature polypeptide coding sequence is nucleotides 77 to 766 of SEQ ID NO: 1.

The nucleotide sequence of SEQ ID NO: 1 or a subsequence thereof; as well as the amino acid sequence of SEQ ID NO: 2 or a fragment thereof, may be used to design a nucleic acid probe to identify and clone DNA encoding polypeptides having cellulolytic enhancing activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other organisms may, therefore, be screened for DNA which hybridizes with the probes described above and which encodes a polypeptide having cellulolytic enhancing activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, or a subsequence thereof, the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1, the genomic DNA sequence comprising the mature polypeptide coding sequence of SEQ ID NO: 1, its complementary strand, or a subsequence thereof, under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 73 to 1259 of SEQ ID NO: 1. In another preferred aspect, the nucleic acid probe is a polynucleotide sequence which encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pTr3337 which is contained in *Escherichia coli* NRRL B-30878, wherein the polynucleotide sequence thereof encodes a polypeptide having cellulolytic enhancing activity. In another preferred aspect, the nucleic acid probe is the mature polypeptide coding region contained in plasmid pTr3337 which is contained in *Escherichia coli* NRRL B-30878.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP40, 1× Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a fourth aspect, the polypeptides having cellulolytic enhancing activity can be artificial variants comprising a conservative substitution, deletion, and/or insertion of one or more amino acids of the mature polypeptide of SEQ ID NO: 2 or a homologous sequence thereof; or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., cellulolytic enhancing activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2 is 10, preferably 9, more preferably 8, more preferably 7, more preferably at most 6, more preferably 5, more preferably 4, even more preferably 3, most preferably 2, and even most preferably 1.

A polypeptide having cellulolytic enhancing activity of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having cellulolytic enhancing activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having cellulolytic enhancing activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having cellulolytic enhancing activity.

In another preferred aspect, the polypeptide is a *Streptococcus equisimilis, Streptococcus pyogenes, Streptococcus uberis,* or *Streptococcus equi* subsp. *Zooepidemicus* polypeptide having cellulolytic enhancing activity.

In another preferred aspect, the polypeptide is a *Streptomyces achromogenes, Streptomyces avermitilis, Streptomyces coelicolor, Streptomyces griseus,* or *Streptomyces lividans* polypeptide having cellulolytic enhancing activity.

The polypeptide having cellulolytic enhancing activity may also be a fungal polypeptide, and more preferably a yeast polypeptide such as a *Candida, Kluyveromyces, Pichia, Saccharomyces, Schizosaccharomyces,* or *Yarrowia* polypeptide having cellulolytic enhancing activity; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* polypeptide having cellulolytic enhancing activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having cellulolytic enhancing activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Coprinus cinereus, Diplodia gossyppina, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Magnaporthe grisea, Mucor miehei, Myceliophthora thermophila, Neurospora crassa, Penicillium purpurogenum, Phanerochaete*

*chrysosporium, Pseudoplectania nigrella, Thermoascus aurantiacus, Thielavia terrestris, Trichoderma harzianum, Trichoderma koningii, Trichoderma longibrachiatum, Trichoderma reesei, Trichoderma viride,* or *Trichophaea saccata* polypeptide having cellulolytic enhancing activity.

In a more preferred aspect, the polypeptide is a *Trichoderma reesei* polypeptide. In a most preferred aspect, the polypeptide is a *Trichoderma reesei* RutC30 (ATCC 56765) polypeptide, e.g., the polypeptide with the amino acid sequence of SEQ ID NO: 2 or fragments thereof, e.g., the mature polypeptide.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides having cellulolytic enhancing activity also include fused polypeptides or cleavable fusion polypeptides in which another polypeptide is fused at the N-terminus or the C-terminus of the polypeptide or fragment thereof having cellulolytic enhancing activity. A fused polypeptide is produced by fusing a nucleotide sequence (or a portion thereof) encoding another polypeptide to a nucleotide sequence (or a portion thereof) encoding a polypeptide h having cellulolytic enhancing activity. Techniques for producing fusion polypeptides are known in the art, and include ligating the coding sequences encoding the polypeptides so that they are in frame and that expression of the fused polypeptide is under control of the same promoter(s) and terminator.

Polynucleotides having nucleotide sequences which encode polypeptides having cellulolytic enhancing activity can be isolated and utilized to practice the methods of the present invention, as described herein.

In a preferred aspect, the nucleotide sequence is set forth in SEQ ID NO: 1. In another more preferred aspect, the nucleotide sequence is the sequence contained in plasmid pTr3337 which is contained in *E. coli* NRRL B-30878. In another preferred aspect, the nucleotide sequence is the mature polypeptide coding region of SEQ ID NO: 1. In another preferred aspect, the nucleotide sequence is nucleotides 77 to 766 of SEQ ID NO: 1. In another more preferred aspect, the nucleotide sequence is the mature polypeptide coding region contained in plasmid pTr3337 which is contained in *E. coli* NRRL B-30878. The present invention also encompasses nucleotide sequences which encode a polypeptide having the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 which encode fragments of SEQ ID NO: 2 that have cellulolytic enhancing activity.

The present invention also relates to mutant polynucleotides comprising at least one mutation in the mature polypeptide coding sequence of SEQ ID NO: 1, in which the mutant nucleotide sequence encodes the mature polypeptide of SEQ ID NO: 2. In a preferred aspect, the mature polypeptide is amino acids 20 to 249 of SEQ ID NO: 2.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Trichoderma,* or another or related organism and thus, for example, may be an allelic or species variant of the polypeptide encoding region of the nucleotide sequence.

In the methods of the present invention, the polynucleotides have nucleotide sequences which have a degree of identity to the mature polypeptide coding sequence of SEQ ID NO: 1 (i.e., nucleotides 388 to 1332) of at least 75%, preferably at least 80%, more preferably at least 85%, even more preferably at least 90%, most preferably at least 95%, and even most preferably at least 96%, 97%, 98%, or 99% identity, which encode an active polypeptide.

Modification of a nucleotide sequence encoding a polypeptide having cellulolytic enhancing activity may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for cellulolytic enhancing activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The polynucleotide may be a polynucleotide encoding a polypeptide having cellulolytic enhancing activity that hybridize under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 1, (ii) the genomic DNA sequence comprising the mature polypeptide coding sequence of SEQ ID NO: 1, or (iii) a complementary strand of (i) or (ii); or allelic variants and subsequences thereof (Sambrook et al., 1989, supra), as defined herein. In a preferred aspect, the mature polypeptide coding sequence is nucleotides 77 to 766 of SEQ ID NO: 1.

Nucleic Acid Constructs

An isolated polynucleotide encoding a polypeptide having cellulolytic enhancing activity may be manipulated in a variety of ways to provide for expression of the polypeptide by constructing a nucleic acid construct comprising an isolated polynucleotide encoding a polypeptide having cellulolytic enhancing activity operably linked to one or more control sequences which direct the expression of the coding sequence in a suitable host cell under conditions compatible with the control sequences. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide having cellulolytic enhancing activity. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and Aspergillus nidulans triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice, i.e., secreted into a culture medium, may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

In a preferred aspect, the signal peptide comprises or consists of amino acids 1 to 19 of SEQ ID NO: 2. In another preferred aspect, the signal peptide coding region comprises or consists of nucleotides 20 to 76 of SEQ ID NO: 1.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The various nucleic acids and control sequences described herein may be joined together to produce a recombinant expression vector comprising a polynucleotide encoding a polypeptide having cellulolytic enhancing activity, a promoter, and transcriptional and translational stop signals. The expression vectors may include one or more convenient restriction sites to allow for insertion or substitution of the nucleotide sequence encoding the polypeptide at such sites. Alternatively, a polynucleotide encoding a polypeptide having cellulolytic enhancing activity may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide encoding a polypeptide having cellulolytic enhancing activity may be inserted into the host cell to increase production of the polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

Recombinant host cells, comprising a polynucleotide encoding a polypeptide having cellulolytic enhancing activity, can be advantageously used in the recombinant production of the polypeptide. A vector comprising such a polynucleotide is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

The bacterial host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus,* and *Oceanobacillus.* Gram negative bacteria include, but not limited to, *E. coli, Pseudomonas, Salmonella, Campylobacter, Helicobacter, Flavobacterium, Fusobacterium, Ilyobacter, Neisseria,* and *Ureaplasma.*

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis,* and *Streptococcus equi* subsp. *Zooepidemicus.*

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus,* and *Streptomyces lividans*.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol. (Praha)* 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98:6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla *Ascomycota, Basidiomycota, Chytridiomycota,* and *Zygomycota* (as defined by Hawksworth et al., In, *Ainsworth and Bisby's Dictionary of The Fungi,* 8th edition, 1995, CAB International, University Press, Cambridge, UK) as well as the *Oomycota* (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarum sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming Fusarium species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide having cellulolytic enhancing activity, comprising (a) cultivating a cell, which in its wild-type form is capable of producing the polypeptide, under conditions conducive for production of the polypeptide; and (b) recovering the polypeptide. Preferably, the cell is of the genus *Trichoderma*, more preferably *Trichoderma reesei*, and most preferably *Trichoderma reesei* RutC30.

The present invention also relates to methods for producing a polypeptide having cellulolytic enhancing activity, comprising (a) cultivating a recombinant host cell under conditions conducive for production of the polypeptide; and (b) recovering the polypeptide.

The present invention also relates to methods for producing a polypeptide having cellulolytic enhancing activity, comprising (a) cultivating a host cell under conditions conducive for production of the polypeptide, wherein the host cell comprises a mutant nucleotide sequence having at least one mutation in the mature polypeptide coding region of SEQ ID NO: 1, wherein the mutant nucleotide sequence encodes a polypeptide which consists of the mature polypeptide of SEQ ID NO: 2, and (b) recovering the polypeptide. In a preferred aspect, the mature polypeptide of SEQ ID NO: 2 is amino acids 20 to 249 of SEQ ID NO: 2.

In the production methods, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides having cellulolytic enhancing activity are detected using the methods described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Cellulolytic Proteins

In the methods of the present invention, the cellulolytic protein may be any protein involved in the processing of cellulosic material to glucose, or hemicellulose to xylose, mannose, galactose, and arabinose, their polymers, or products derived from them as described below. The cellulolytic protein may be a monocomponent preparation, e.g., a cellulase, a multicomponent preparation, e.g., endoglucanase, cellobiohydrolase, glucohydrolase, beta-glucosidase, as defined below, or a combination of multicomponent and monocomponent protein preparations. The cellulolytic proteins may have activity, i.e., hydrolyze cellulose, either in the acid, neutral, or alkaline pH-range.

The cellulolytic protein may be of fungal or bacterial origin, which may be obtainable or isolated and purified from microorganisms which are known to be capable of producing cellulolytic enzymes, e.g., species of *Bacillus*, *Pseudomonas*, *Humicola*, *Coprinus*, *Thielavia*, *Fusarium*, *Myceliophthora*, *Acremonium*, *Cephalosporium*, *Scytalidium*, *Penicillium* or *Aspergillus* (see, for example, EP 458162), especially those produced by a strain selected from *Humicola insolens* (reclassified as *Scytalidium thermophilum*, see for example, U.S. Pat. No. 4,435,307), *Coprinus cinereus*, *Fusarium oxysporum*, *Myceliophthora thermophila*, *Meripilus giganteus*, *Thielavia terrestris*, *Acremonium* sp., *Acremonium persicinum*, *Acremonium acremonium*, *Acremonium brachypenium*, *Acremonium dichromosporum*, *Acremonium obclavatum*, *Acremonium pinkertoniae*, *Acremonium roseogriseum*, *Acremonium incoloratum*, and *Acremonium furatum*; preferably from *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic proteins may also be obtained from *Trichoderma* (particularly *Trichoderma viride*, *Trichoderma reesei*, and *Trichoderma koningii*), alkalophilic *Bacillus* (see, for example, U.S. Pat. No. 3,844,890 and EP 458162), and *Streptomyces* (see, for example, EP 458162). Chemically modified or protein engineered mutants of cellulolytic proteins may also be used.

Especially suitable cellulolytic proteins are the alkaline or neutral cellulases. Examples of such cellulases are cellulases described in EP 495,257, EP 531,372, WO 96/11262, WO 96/29397, WO 98/08940. Other examples are cellulase variants such as those described in WO 94/07998, EP 531,315, U.S. Pat. Nos. 4,435,307, 5,457,046, 5,648,263, 5,686,593, 5,691,178, 5,763,254, 5,776,757, WO 89/09259, WO 95/24471, WO 98/12307, and The cellulolytic proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and cellulolytic protein production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of a cellulolytic protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the cellulolytic protein or cellulolytic enhancing protein to be expressed or isolated.

The resulting cellulolytic proteins produced by the methods described above may be recovered from the fermentation medium and purified by conventional procedures as described herein.

Cellulolytic protein may hydrolyze or hydrolyzes carboxymethyl cellulose (CMC), thereby decreasing the viscosity of the incubation mixture. The resulting reduction in viscosity may be determined by a vibration viscosimeter (e.g., MIVI 3000 from Sofraser, France). Determination of cellulase activity, measured in terms of Cellulase Viscosity Unit (CEVU), quantifies the amount of catalytic activity present in a sample by measuring the ability of the sample to reduce the viscosity of a solution of carboxymethyl cellulose (CMC). The assay is performed at the temperature and pH suitable for the cellulolytic protein and substrate. For Celluclast™ (Novozymes A/S, Bagsværd, Denmark) the assay is carried out at 40° C. in 0.1 M phosphate pH 9.0 buffer for 30 minutes with CMC as substrate (33.3 g/L carboxymethyl cellulose Hercules 7 LFD) and an enzyme concentration of approximately 3.3-4.2 CEVU/ml. The CEVU activity is calculated relative to a declared enzyme standard, such as CELLUZYME™ Standard 17-1194 (obtained from Novozymes A/S, Bagsværd, Denmark).

Examples of cellulolytic preparations suitable for use in the present invention include, for example, CELLUCLAST™ (available from Novozymes A/S) and NOVOZYM™ 188 (available from Novozymes A/S). Other commercially available preparations comprising cellulase which may be used include CELLUZYME™, CEREFLO™ and ULTRAFLO™ (Novozymes A/S), LAMINEX™ and SPEZYME™ CP (Genencor Int.), and ROHAMENT™ 7069 W (Röhm GmbH). The cellulase enzymes are added in amounts effective from about 0.001% to about 5.0% wt. of solids, more preferably from about 0.025% to about 4.0% wt. of solids, and most preferably from about 0.005% to about 2.0% wt. of solids.

As mentioned above, the cellulolytic proteins or cellulolytic enhancing proteins used in the methods of the present invention may be monocomponent preparations, i.e., a component essentially free of other cellulolytic components. The single component may be a recombinant component, i.e., produced by cloning of a DNA sequence encoding the single component and subsequent cell transformed with the DNA sequence and expressed in a host (see, for example, WO 91/17243 and WO 91/17244). Other examples of monocomponent cellulolytic proteins include, but are not limited to, those disclosed in JP-07203960-A and WO-9206209. The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

Examples of monocomponent cellulolytic proteins useful in practicing the methods of the present invention include, but are not limited to, endoglucanase, cellobiohydrolase, glucohydrolase, and beta-glucosidase.

The term "endoglucanase" is defined herein as an endo-1, 4-(1,3;1,4)-beta-D-glucan 4-glucanohydrolase (E.C. No. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, Pure and Appl. Chem. 59: 257-268.

The exo-1,4-beta-D-glucanases include both cellobiohydrolases and glucohydrolases. For purposes of the present invention, exoglucanase activity is determined according to the procedure described by Himmel et al., 1986, J. Biol. Chem. 261: 12948-12955.

The term "cellobiohydrolase" is defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain. For purposes of the present invention, cellobiohydrolase activity is determined according to the procedures described by Lever et al., 1972, Anal. Biochem. 47: 273-279 and by van Tilbeurgh et al., 1982, FEBS Letters 149: 152-156; van Tilbeurgh and Claeyssens, 1985, FEBS Letters 187: 283-288. In the present invention, the Lever et al. method was employed to assess hydrolysis of cellulose in corn stover, while the method of van Tilbeurgh et al. was used to determine the cellobiohydrolase activity on a fluorescent disaccharide derivative.

The term "glucohydrolase" is defined herein as a 1,4-beta-D-glucan glucohydrolase (E.C. 3.2.1.74), which catalyzes the hydrolysis of 1,4-linkages (O-glycosyl bonds) in 1,4-beta-D-glucans so as to remove successive glucose units.

The term "beta-glucosidase" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, J. Basic Microbiol. 42: 55-66, except different conditions were employed as described herein. One unit of beta-glucosidase activity is defined as 1.0 µmole of p-nitrophenol produced per minute at 50° C., pH 5 from 4 mM p-nitrophenyl-beta-D-glucopyranoside as substrate in 100 mM sodium citrate, 0.01% Tween-20.

Processing of Cellulosic Material

The methods of the present invention can be used to process a cellulosic material to many useful substances, e.g., chemicals and fuels. In addition to ethanol, some commodity and specialty chemicals that can be produced from cellulose include xylose, acetone, acetate, glycine, lysine, organic acids (e.g., lactic acid), 1,3-propanediol, butanediol, glycerol, ethylene glycol, furfural, polyhydroxyalkanoates, and cis, cis-muconic acid (Lynd, L. R., Wyman, C. E., and Gerngross, T. U., 1999, Biocommodity Engineering, Biotechnol. Prog., 15: 777-793; Philippidis, G. P., 1996, Cellulose bioconversion technology, in Handbook on Bioethanol: Production and Utilization, Wyman, C. E., ed., Taylor & Francis, Washington, DC, 179-212; and Ryu, D. D. Y., and Mandels, M., 1980, Cellulases: biosynthesis and applications, Enz. Microb. Technol., 2: 91-102). Potential coproduction benefits extend beyond the synthesis of multiple organic products from fermentable carbohydrate. Lignin-rich residues remaining after biological processing can be converted to lignin-derived chemicals, or used for power production.

Conventional methods used to process the cellulosic material in accordance with the methods of the present invention are well understood to those skilled in the art. The methods of the present invention may be implemented using any conventional biomass processing apparatus configured to operate in accordance with the invention.

Such an apparatus may include a batch-stirred reactor, a continuous flow stirred reactor with ultrafiltration, a continuous plug-flow column reactor (Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153).

The conventional methods include, but are not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to glucose and then ferment glucose to ethanol. In SSF, the enzymatic hydrolysis of cellulose and the fermentation of glucose to ethanol is combined in one step (Philippidis, G. P., 1996, Cellulose bioconversion technology, in *Handbook on Bioethanol: Production and Utilization*, Wyman, C. E., ed., Taylor & Francis, Washington, DC, 179-212). SSCF includes the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577).

"Fermentation" or "fermentation process" refers to any fermentation process or any process comprising a fermentation step. A fermentation process includes, without limitation, fermentation processes used to produce fermentation products including alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)). Fermentation processes also include fermentation processes used in the consumable alcohol industry (e.g., beer and wine), dairy industry (e.g., fermented dairy products), leather industry, and tobacco industry.

The polypeptide having cellulolytic enhancing activity may be in the form of a crude fermentation broth with or without the cells or in the form of a semi-purified or purified enzyme preparation. The cellulolytic enhancing protein may be a monocomponent preparation, e.g., a Family 61 protein, a multicomponent protein preparation, e.g., a number of Family 61 proteins, or a combination of multicomponent and monocomponent protein preparations.

The substance can be any substance derived from the fermentation. In a preferred aspect, the substance is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the substance is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid: In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the substance is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the substance is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the substance is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Production of a substance from cellulosic material typically requires four major steps. These four steps are pretreatment, enzymatic hydrolysis, fermentation, and recovery. Exemplified below is a process for producing ethanol, but it will be understood that similar processes can be used to produce other substances, for example, the substances described above.

Pretreatment. In the pretreatment or pre-hydrolysis step, the cellulosic material is heated to break down the lignin and carbohydrate structure, solubilize most of the hemicellulose, and make the cellulose fraction accessible to cellulolytic enzymes. The heating is performed either directly with steam or in slurry where a catalyst may also be added to the material to speed up the reactions. Catalysts include strong acids, such as sulfuric acid and $SO_2$, or alkali, such as sodium hydroxide. The purpose of the pre-treatment stage is to facilitate the penetration of the enzymes and microorganisms. Cellulosic biomass may also be subject to a hydrothermal steam explosion pre-treatment (See U.S. Patent Application No. 20020164730).

Saccharification. In the enzymatic hydrolysis step, also known as saccharification, enzymes as described herein are added to the pretreated material to convert the cellulose fraction to glucose and/or other sugars. The saccharification is generally performed in stirred-tank reactors or fermentors under controlled pH, temperature, and mixing conditions. A saccharification step may last up to 200 hours. Saccharification may be carried out at temperatures from about 30° C. to about 65° C., in particular around 50° C., and at a pH in the range between about 4 and about 5, especially around pH 4.5. To produce glucose that can be metabolized by yeast, the hydrolysis is typically performed in the presence of a beta-glucosidase.

Fermentation. In the fermentation step, sugars, released from the cellulosic material as a result of the pretreatment and enzymatic hydrolysis steps, are fermented to ethanol by a fermenting organism, such as yeast. The fermentation can also be carried out simultaneously with the enzymatic hydrolysis in the same vessel, again under controlled pH, temperature, and mixing conditions. When saccharification and fermentation are performed simultaneously in the same vessel, the process is generally termed simultaneous saccharification and fermentation or SSF.

Any suitable cellulosic substrate or raw material may be used in a fermentation process in practicing the present invention. The substrate is generally selected based on the desired fermentation product, i.e., the substance to be obtained from the fermentation, and the process employed, as is well known in the art. Examples of substrates suitable for use in the methods of present invention, include cellulose-containing materials, such as wood or plant residues or low molecular sugars DP1-3 obtained from processed cellulosic material that can be metabolized by the fermenting microorganism, and which may be supplied by direct addition to the fermentation medium.

The term "fermentation medium" will be understood to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism suitable for use in a desired fermentation process. Suitable fermenting microorganisms according to the invention are able to ferment, i.e., convert, sugars, such as glucose, xylose, arabinose, mannose, galactose, or oligosaccharides directly or indirectly into the desired fermentation product. Examples of fermenting microorganisms include fungal organisms, such as yeast. Preferred yeast includes strains of the *Saccharomyces* spp., and in particular, *Saccharomyces cerevisiae*. Commercially available yeast include, e.g., Red Star®/™/ Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida pseudotropicalis*. In another more preferred aspect, the yeast is *Candida brassicae*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, DC, 179-212).

Bacteria that can efficiently ferment glucose to ethanol include, for example, *Zymomonas mobilis* and *Clostridium thermocellum* (Philippidis, 1996, supra).

It is well known in the art that the organisms described above can also be used to produce other substances, as described herein.

The cloning of heterologous genes in *Saccharomyces cerevisiae* (Chen, Z., Ho, N. W. Y., 1993, Cloning and improving the expression of *Pichia stipitis* xylose reductase gene in *Saccharomyces cerevisiae*, *Appl. Biochem. Biotechnol.* 39-40: 135-147; Ho, N. W. Y., Chen, Z, Brainard, A. P., 1998, Genetically engineered Saccharomyces yeast capable of effectively cofermenting glucose and xylose, *Appl. Environ. Microbiol.* 64: 1852-1859), or in bacteria such as *Escherichia coli* (Beall, D. S., Ohta, K., Ingram, L. O., 1991, Parametric studies of ethanol production from xylose and other sugars by recombinant *Escherichia coli*, *Biotech. Bioeng.* 38: 296-303), *Klebsiella oxytoca* (Ingram, L. O., Gomes, P. F., Lai, X., Moniruzzaman, M., Wood, B. E., Yomano, L. P., York, S. W., 1998, Metabolic engineering of bacteria for ethanol production, *Biotechnol. Bioeng.* 58: 204-214), and *Zymomonas mobilis* (Zhang, M., Eddy, C., Deanda, K., Finkelstein, M., and Picataggio, S., 1995, Metabolic engineering of a pentose metabolism pathway in ethanologenic *Zymomonas mobilis, Science* 267: 240-243; Deanda, K., Zhang, M., Eddy, C., and Picataggio, S., 1996, Development of an arabinose-fermenting *Zymomonas mobilis* strain by metabolic pathway engineering, *Appl. Environ. Microbiol.* 62: 4465-4470) has led to the construction of organisms capable of converting hexoses and pentoses to ethanol (cofermentation).

Yeast or another microorganism typically is added to the degraded cellulose or hydrolysate and the fermentation is performed for about 24 to about 96 hours, such as about 35 to about 60 hours. The temperature is typically between about 26° C. to about 40° C., in particular at about 32° C., and at about pH 3 to about pH 6, in particular around pH 4-5.

In a preferred aspect, yeast or another microorganism is applied to the degraded cellulose or hydrolysate and the fermentation is performed for about 24 to about 96 hours, such as typically 35-60 hours. In a preferred aspect, the temperature is generally between about 26 to about 40° C., in particular about 32° C., and the pH is generally from about pH 3 to about pH 6, preferably around pH 4-5. Yeast or another microorganism is preferably applied in amounts of approximately $10^5$ to $10^{12}$, preferably from approximately $10^7$ to $10^{10}$, especially approximately $5 \times 10^7$ viable count per ml of fermentation broth. During an ethanol producing phase the yeast cell count should preferably be in the range from approximately $10^7$ to $10^{10}$, especially around approximately $2 \times 10^8$. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

The most widely used process in the art is the simultaneous saccharification and fermentation (SSF) process where there is no holding stage for the saccharification, meaning that yeast and enzyme are added together.

For ethanol production, following the fermentation the mash is distilled to extract the ethanol. The ethanol obtained according to the process of the invention may be used as, e.g., fuel ethanol, drinking ethanol, i.e., potable neutral spirits, or industrial ethanol.

A fermentation stimulator may be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, e.g., Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Recovery. The alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

For other substances, any method known in the art can be used including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, distillation, or extraction.

In the methods of the present invention, the cellulolytic protein(s) and cellulolytic enhancing polypeptide(s) may be supplemented by one or more additional enzyme activities to improve the degradation of the cellulosic material. Preferred additional enzymes are hemicellulases, esterases (e.g., lipases, phospholipases, and/or cutinases), proteases, laccases, peroxidases, or mixtures thereof.

In the methods of the present invention, the additional enzyme(s) may be added prior to or during fermentation, including during or after the propagation of the fermenting microorganism(s).

The enzymes referenced herein may be derived or obtained from any suitable origin, including, bacterial, fungal, yeast or mammalian origin. The term "obtained" means herein that the enzyme may have been isolated from an organism which naturally produces the enzyme as a native enzyme. The term "obtained" also means herein that the enzyme may have been produced recombinantly in a host organism, wherein the recombinantly produced enzyme is either native or foreign to the host organism or has a modified amino acid sequence, e.g., having one or more amino acids which are deleted, inserted and/or substituted, i.e., a recombinantly produced enzyme which is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

The enzymes may also be purified. The term "purified" as used herein covers enzymes free from other components from the organism from which it is derived. The term "purified" also covers enzymes free from components from the native organism from which it is obtained. The enzymes may be purified, with only minor amounts of other proteins being present. The expression "other proteins" relate in particular to other enzymes. The term "purified" as used herein also refers to removal of other components, particularly other proteins and most particularly other enzymes present in the cell of origin of the enzyme of the invention. The enzyme may be "substantially pure polypeptide," that is, free from other components from the organism in which it is produced, that is, for example, a host organism for recombinantly produced enzymes.

The enzymes used in the present invention may be in any form suitable for use in the processes described herein, such as, for example, a crude fermentation broth with or without cells, a dry powder or granulate, a non-dusting granulate, a liquid, a stabilized liquid, or a protected enzyme. Granulates may be produced, e.g., as disclosed in U.S. Pat. Nos. 4,106,991 and 4,661,452, and may optionally be coated by process known in the art. Liquid enzyme preparations may, for instance, be stabilized by adding stabilizers such as a sugar, a sugar alcohol or another polyol, and/or lactic acid or another organic acid according to established process. Protected enzymes may be prepared according to the process disclosed in EP 238,216.

Hemicellulases

Enzymatic hydrolysis of hemicelluloses can be performed by a wide variety of fungi and bacteria. Similar to cellulose degradation, hemicellulose hydrolysis requires coordinated action of many enzymes. Hemicellulases can be placed into three general categories: the endo-acting enzymes that attack internal bonds within the polysaccharide chain, the exo-acting enzymes that act processively from either the reducing or nonreducing end of polysaccharide chain, and the accessory enzymes, acetylesterases and esterases that hydrolyze lignin glycoside bonds, such as coumaric acid esterase and ferulic acid esterase (Wong, K. K. Y., Tan, L. U. L., and Saddler, J. N., 1988, Multiplicity of β-1,4-xylanase in microorganisms: Functions and applications, *Microbiol. Rev.* 52: 305-317; Tenkanen, M., and Poutanen, K., 1992, Significance of esterases in the degradation of xylans, in *Xylans and Xylanases,* Visser, J., Beldman, G., Kuster-van Someren, M. A., and Voragen, A. G. J., eds., Elsevier, New York, N.Y., 203-212; Coughlan, M. P., and Hazlewood, G. P., 1993, *Hemicellulose and hemicellulases,* Portland, London, UK; Brigham, J. S., Adney, W. S., and Himmel, M. E., 1996, Hemicellulases: Diversity and applications, in *Handbook on Bioethanol: Production and Utilization,* Wyman, C. E., ed., Taylor & Francis, Washington, DC, 119-141).

Hemicellulases include xylanases, arabinofuranosidases, acetyl xylan esterase, glucuronidases, endo-galactanase, mannanases, endo or exo arabinases, exo-galactanses, and mixtures thereof. Examples of endo-acting hemicellulases and ancillary enzymes include endoarabinanase, endoarabinogalactanase, endoglucanase, endomannanase, endoxylanase, and feraxan endoxylanase. Examples of exo-acting hemicellulases and ancillary enzymes include α-L-arabinosidase, β-L-arabinosidase, α-1,2-L-fucosidase, α-D-galactosidase, β-D-galactosidase, β-D-glucosidase, β-D-glucuronidase, β-D-mannosidase, β-D-xylosidase, exoglucosidase, exocellobiohydrolase, exomannobiohydrolase, exomannanase, exoxylanase, xylan α-glucuronidase, and coniferin β-glucosidase. Examples of esterases include acetyl esterases (acetylgalactan esterase, acetylmannan esterase, and acetylxylan esterase) and aryl esterases (coumaric acid esterase and ferulic acid esterase).

Preferably, the hemicellulase is an exo-acting hemicellulase, and more preferably, an exo-acting hemicellulase which has the ability to hydrolyze hemicellulose under acidic conditions of below pH 7. An example of a hemicellulase suitable for use in the present invention includes VISCOZYME™ (available from Novozymes A/S, Denmark). The hemicellulase is added in an effective amount from about 0.001% to about 5.0% wt. of solids, more preferably from about 0.025% to about 4.0% wt. of solids, and most preferably from about 0.005% to about 2.0% wt. of solids.

A xylanase (E.C. 3.2.1.8) may be obtained from any suitable source, including fungal and bacterial organisms, such as *Aspergillus, Disporotrichum, Penicillium, Neurospora, Fusarium, Trichoderma, Humicola, Thermomyces,* and *Bacillus.* Preferred commercially available preparations comprising xylanase include SHEARZYME®, BIOFEED WHEAT®, BIO-FEED Plus® L, CELLUCLAST®, ULTRAFLO®, VISCOZYME®, PENTOPAN MONO® BG, and PULPZYME® HC (Novozymes A/S); and LAMINEX® and SPEZYME® CP (Genencor Int.).

Esterases

Esterases that can be used for bioconversion of cellulose include acetyl esterases such as acetylgalactan esterase, acetylmannan esterase, and acetylxylan esterase, and esterases that hydrolyze lignin glycoside bonds, such as coumaric acid esterase and ferulic acid esterase.

As used herein, an "esterase" also known as a carboxylic ester hydrolyase, refers to enzymes acting on ester bonds, and includes enzymes classified in EC 3.1.1 Carboxylic Ester Hydrolases according to Enzyme Nomenclature (*Enzyme Nomenclature,* 1992, Academic Press, San Diego, Calif., with Supplement 1 (1993), Supplement 2 (1994), Supplement 3 (1995), Supplement 4 (1997) and Supplement 5, in *Eur. J. Biochem.* 223: 1-5, 1994; *Eur. J. Biochem.* 232: 1-6, 1995; *Eur. J. Biochem.* 237: 1-5, 1996; *Eur. J. Biochem.* 250: 1-6, 1997, and *Eur. J. Biochem.* 264: 610-650, 1999; respectively). Non-limiting examples of esterases include arylesterase, triacylglycerol lipase, acetylesterase, acetylcholinesterase, cholinesterase, tropinesterase, pectinesterase, sterol esterase, chlorophyllase, L-arabinonolactonase, gluconolactonase, uronolactonase, tannase, retinyl-palmitate esterase, hydroxybutyrate-dimer hydrolase, acylglycerol lipase, 3-oxoadipate enol-lactonase, 1,4-lactonase, galactolipase, 4-pyridoxolactonase, acylcarnitine hydrolase, aminoacyl-tRNA hydrolase, D-arabinonolactonase, 6-phosphogluconolactonase, phospholipase A1, 6-acetylglucose deacetylase, lipoprotein lipase, dihydrocoumarin lipase, limonin-D-ring-lactonase, steroid-lactonase, triacetate-lactonase, actinomycin lactonase, orsellinate-depside hydrolase, cephalosporin-C deacetylase, chlorogenate hydrolase, alpha-amino-acid esterase, 4-methyloxaloacetate esterase, carboxymethylenebutenolidase, deoxylimonate A-ring-lactonase, 2-acetyl-1-alkylglycerophosphocholine esterase, fusarinine-C ornithinesterase, sinapine esterase, wax-ester hydrolase, phorbol-diester hydrolase, phosphatidylinositol deacylase, sialate O-acetylesterase, acetoxybutynylbithiophene deacetylase, acetylsalicylate deacetylase, methylumbelliferyl-acetate deacetylase, 2-pyrone-4,6-dicarboxylate lactonase, N-acetylgalactosaminoglycan deacetylase, juvenile-hormone esterase, bis(2-ethylhexyl)phthalate esterase, protein-glutamate methylesterase, 11-cis-retinyl-palmitate hydrolase, all-trans-retinyl-palmitate hydrolase, L-rhamnono-1,4-lactonase, 5-(3,4-diacetoxybut-1-ynyl)-2,2'-bithiophene deacetylase, fatty-acyl-ethyl-ester synthase, xylono-1,4-lactonase, N-acetylglucosaminylphosphatidylinositol deacetylase, cetraxate benzylesterase, acetylalkylglycerol acetylhydrolase, and acetylxylan esterase.

Preferred esterases for use in the present invention are lipolytic enzymes, such as, lipases (classified as EC 3.1.1.3, EC 3.1.1.23, and/or EC 3.1.1.26) and phospholipases (classified as EC 3.1.1.4 and/or EC 3.1.1.32, including lysophospholipases classified as EC 3.1.1.5). Other preferred esterases are cutinases (classified as EC 3.1.1.74).

The esterase may be added in an amount effective to obtain the desired benefit to improve the performance of the fermenting microorganism, for example, to change the lipid composition/concentration inside and/or outside of the fermenting microorganism or in the cell membrane of the fermenting microorganism, to result in an improvement in the movement of solutes into and/or out of the fermenting microorganisms during fermentation and/or to provide more metabolizable energy sources (such as, for example, by converting components, such as, oil from the corn substrate, to components useful the fermenting microorganism, e.g., unsaturated fatty acids and glycerol), to increase ethanol yield. Examples of effective amounts of esterase are from about 0.01 to about 400 LU/g DS (Dry Solids). Preferably, the esterase is used in an amount of about 0.1 to about 100 LU/g DS, more preferably about 0.5 to about 50 LU/g DS, and even more preferably about 1 to about 20 LU/g DS. Further optimization of the amount of esterase can hereafter be obtained using standard procedures known in the art.

One Lipase Unit (LU) is the amount of enzyme which liberates 1.0 μmol of titratable fatty acid per minute with tributyrin as substrate and gum arabic as an emulsifier at 30(C, pH 7.0 (phosphate buffer).

In a preferred aspect, the esterase is a lipolytic enzyme, more preferably, a lipase. As used herein, a "lipolytic enzyme" refers to lipases and phospholipases (including lyso-phospholipases). The lipolytic enzyme is preferably of microbial origin, in particular of bacterial, fungal or yeast origin. The lipolytic enzyme used may be derived from any source, including, for example, a strain of *Absidia*, in particular *Absidia blakesleena* and *Absidia corymbifera*, a strain of *Achromobacter*, in particular *Achromobacter iophagus*, a strain of *Aeromonas*, a strain of *Alternaria*, in particular *Alternaria brassiciola*, a strain of *Aspergillus*, in particular *Aspergillus niger*, *Aspergillus oryzae*, *Aspergillus fumigatus*, and *Aspergillus flavus*, a strain of *Achromobacter*, in particular *Achromobacter iophagus*, a strain of *Aureobasidium*, in particular *Aureobasidium pullulans*, a strain of *Bacillus*, in particular *Bacillus pumilus*, *Bacillus stearothermophilus*, and *Bacillus subtilis*, a strain of *Beauveria*, a strain of *Brochothrix*, in particular *Brochothrix thermosohata*, a strain of *Candida*, in particular *Candida cylindracea* (*Candida rugosa*), *Candida paralipolytica*, and *Candida antarctica*, a strain of *Chromobacter*, in particular *Chromobacter viscosum*, a strain of *Coprinus*, in particular *Coprinus cinereus*, a strain of *Fusarium*, in particular *Fusarium graminearum*, *Fusarium oxysporum*, *Fusarium solani*, *Fusarium solani pisi*, *Fusarium roseum culmorum*, and *Fusarium venenatum*, a strain of *Geotricum*, in particular *Geotricum penicillatum*, a strain of *Hansenula*, in particular *Hansenula anomala*, a strain of *Humicola*, in particular *Humicola brevispora*, *Humicola brevis* var. *thermoidea*, and *Humicola insolens*, a strain of *Hyphozyma*, a strain of *Lactobacillus*, in particular *Lactobacillus curvatus*, a strain of *Metarhizium*, a strain of *Mucor*, a strain of *Paecilomyces*, a strain of *Penicillium*, in particular *Penicillium cyclopium*, *Penicillium crustosum* and *Penicillium expansum*, a strain of *Pseudomonas* in particular *Pseudomonas aeruginosa*, *Pseudomonas alcaligenes*, *Pseudomonas cepacia* (syn. *Burkholderia cepacia*), *Pseudomonas fluorescens*, *Pseudomonas fragi*, *Pseudomonas maltophilia*, *Pseudomonas mendocina*, *Pseudomonas mephitica lipolytica*, *Pseudomonas alcaligenes*, *Pseudomonas plantari*, *Pseudomonas pseudoalcaligenes*, *Pseudomonas putida*, *Pseudomonas stutzeri*, and *Pseudomonas wisconsinensis*, a strain of *Rhizooctonia*, in particular *Rhizooctonia solani*, a strain of *Rhizomucor*, in particular *Rhizomucor miehei*, a strain of *Rhizopus*, in particular *Rhizopus japonicus*, *Rhizopus microsporus*, and *Rhizopus nodosus*, a strain of *Rhodosporidium*, in particular *Rhodosporidium toruloides*, a strain of *Rhodotorula*, in particular *Rhodotorula glutinis*, a strain of *Sporobolomyces*, in particular *Sporobolomyces shibatanus*, a strain of *Thermomyces*, in particular *Thermomyces lanuginosus* (formerly *Humicola lanuginosa*), a strain of *Thiarosporella*, in particular *Thiarosporella phaseolina*, a strain of *Trichoderma*, in particular, *Trichoderma harzianum* and *Trichoderma reesei*, and/or a strain of *Verticillium*.

In a preferred aspect, the lipolytic enzyme is derived from a strain of *Aspergillus*, *Achromobacter*, *Bacillus*, *Candida*, *Chromobacter*, *Fusarium*, *Humicola*, *Hyphozyma*, *Pseudomonas*, *Rhizomucor*, *Rhizopus*, or *Thermomyces*.

In more preferred aspects, the lipolytic enzyme is a lipase. Lipases may be applied herein for their ability to modify the structure and composition of triglyceride oils and fats in the fermentation media (including fermentation yeast), for example, resulting from a corn substrate. Lipases catalyze different types of triglyceride conversions, such as hydrolysis, esterification, and transesterification. Suitable lipases include acidic, neutral, and basic lipases, as are well-known in the art, although acidic lipases (such as, e.g., the lipase G AMANO 50, available from Amano) appear to be more effective at lower concentrations of lipase as compared to either neutral or basic lipases. Preferred lipases for use in the present invention include *Candida antarcitca* lipase and *Candida cylindracea* lipase. More preferred lipases are purified lipases such as *Candida antarcitca* lipase (lipase A), *Candida antarcitca* lipase (lipase B), *Candida cylindracea* lipase, and *Penicillium camembertii* lipase.

The lipase may be the one disclosed in EP 258,068-A or may be a lipase variant such as a variant disclosed in WO 00/60063 or WO 00/32758, hereby incorporated by reference.

Lipases are preferably added in amounts from about 1 to about 400 LU/g DS, preferably about 1 to about 10 LU/g DS, and more preferably about 1 to about 5 LU/g DS.

In another preferred aspect, the esterase is a cutinase. Cutinases are enzymes which are able to degrade cutin. The cutinase may be derived from any source. In a preferred aspect, the cutinase is derived from a strain of *Aspergillus*, in particular *Aspergillus oryzae*, a strain of *Alternaria*, in particular *Alternaria brassiciola*, a strain of *Fusarium*, in particular *Fusarium solani*, *Fusarium solani pisi*, *Fusarium roseum culmorum*, or *Fusarium roseum sambucium*, a strain of *Helminthosporum*, in particular *Helminthosporum sativum*, a strain of *Humicola*, in particular *Humicola insolens*, a strain of *Pseudomonas*, in particular *Pseudomonas mendocina* or *Pseudomonas putida*, a strain of *Rhizooctonia*, in particular *Rhizooctonia solani*, a strain of *Streptomyces*, in particular *Streptomyces scabies*, or a strain of *Ulocladium*, in particular *Ulocladium consortiale*. In a most preferred aspect the cutinase is derived from a strain of *Humicola insolens*, in particular the strain *Humicola insolens* DSM 1800. *Humicola insolens* cutinase is described in WO 96/13580, which is hereby incorporated by reference. The cutinase may be a variant such as one of the variants disclosed in WO 00/34450 and WO 01/92502, which are hereby incorporated by reference. Preferred cutinase variants include variants listed in Example 2 of WO 01/92502 which are hereby specifically incorporated by reference. An effective amount of cutinase is from about 0.01 to about 400 LU/g DS, preferably from about 0.1 to about 100 LU/g DS, and more preferably from about 1 to about 50 LU/g DS. Further optimization of the amount of cutinase can hereafter be obtained using standard procedures known in the art.

In another preferred aspect, the esterase is a phospholipase. As used herein, the term "phospholipase" is an enzyme which has activity towards phospholipids, e.g., hydrolytic activity. Phospholipids, such as lecithin or phosphatidylcholine, consist of glycerol esterified with two fatty acids in an outer (sn-1) and the middle (sn-2) positions and esterified with phosphoric acid in the third position. The phosphoric acid may be esterified to an amino-alcohol. Several types of phospholipase activity can be distinguished, including phospholipases A1 and A2 which hydrolyze one fatty acyl group (in the sn-1 and sn-2 position, respectively) to form lysophospholipid; and lysophospholipase (or phospholipase B) which hydrolyzes the remaining fatty acyl group in lysophospholipid. Phospholipase C and phospholipase D (phosphodiesterases) release diacyl glycerol or phosphatidic acid respectively.

The term "phospholipase" includes enzymes with phospholipase activity, e.g., phospholipase A (A1 or A2), phospholipase B activity, phospholipase C activity, or phospholipase D activity. The term "phospholipase A" as used herein is intended to cover an enzyme with phospholipase A1 and/or phospholipase A2 activity. The phospholipase activity may be provided by enzymes having other activities as well, such as, e.g., a lipase with phospholipase activity. The phospholipase activity may, for example, be from a lipase with phospholipase side activity. In other aspects, the phospholipase enzyme activity is provided by an enzyme having essentially only phospholipase activity and wherein the phospholipase enzyme activity is not a side activity.

The phospholipase may be of any origin, for example, of animal origin (e.g., mammalian, for example, bovine or porcine pancreas), or snake venom or bee venom. Alternatively, the phospholipase may be of microbial origin, for example, from filamentous fungi, yeast or bacteria, such as *Aspergillus*, e.g., *A. awamori, A. foetidus, A. japonicus, A. niger*, or *A. oryzae, Dictyostelium*, e.g., *D. discoideum; Fusarium*, e.g., *F. culmorum, F. graminearum, F. heterosporum, F. solani, F. oxysporum*, or *F. venenatum; Mucor*, e.g., *M. javanicus, M. mucedo*, or *M. subtilissimus; Neurospora*, e.g., *N. crassa; Rhizomucor*, e.g., *R. pusillus; Rhizopus*, e.g., *R. arrhizus, R. japonicus*, or *R. stolonifer; Sclerotinia*, e.g., *S. libertiana; Trichophyton*, e.g., *T. rubrum; Whetzelinia*, e.g., *W. sclerotiorum; Bacillus*, e.g., *B. megaterium* or *B. subtilis; Citrobacter*, e.g., *C. freundii; Enterobacter*, e.g., *E. aerogenes* or *E. cloacae; Edwardsiella, E. tarda; Erwinia*, e.g., *E. herbicola; Escherichia*, e.g., *E. coli; Klebsiella*, e.g., *K. pneumoniae; Proteus*, e.g., *P. vulgaris; Providencia*, e.g., *P. stuartii, Salmonella*, e.g., *S. typhimurium; Serratia*, e.g., *S. liquefasciens, S. marcescens; Shigella*, e.g., *S. flexneri; Streptomyces*, e.g., *S. violeceoruber*; or *Yersinia*, e.g., *Y. enterocolitica*.

Preferred commercial phospholipases include LECITASE™ and LECITASE™ ULTRA (available from Novozymes A/S, Denmark).

An effective amount of phospholipase is from about 0.01 to about 400 LU/g DS, preferably from about 0.1 to about 100 LU/g DS, and more preferably from about 1 to about 50 LU/g DS. Further optimization of the amount of phospholipase can hereafter be obtained using standard procedures known in the art.

Proteases

In another preferred aspect of the invention, at least one surfactant and at least one carbohydrate generating enzyme is used in combination with at least one protease. The protease may be used, e.g., to digest protein to produce free amino nitrogen (FAN). Such free amino acids function as nutrients for the yeast, thereby enhancing the growth of the yeast and, consequently, the production of ethanol.

The fermenting microorganism for use in a fermentation process may be produced by propagating the fermenting microorganism in the presence of at least one protease. Although not limited to any one theory of operation, it is believed that the propagation of the fermenting microorganism with an effective amount of at least one protease reduces the lag time of the fermenting microorganism when the fermenting microorganism is subsequently used in a fermentation process as compared to a fermenting microorganism that was propogated under the same conditions without the addition of the protease. The action of the protease in the propagation process is believed to directly or indirectly result in the suppression or expression of genes which are detrimental or beneficial, respectively, to the fermenting microorganism during fermentation, thereby decreasing lag time and resulting in a faster fermentation cycle.

Proteases are well known in the art and refer to enzymes that catalyze the cleavage of peptide bonds. Suitable proteases include fungal and bacterial proteases. Preferred proteases are acidic proteases, i.e., proteases characterized by the ability to hydrolyze proteins under acidic conditions below pH 7. Suitable acid fungal proteases include fungal proteases derived from *Aspergillus, Mucor, Rhizopus, Candida, Coriolus, Endothia, Enthomophtra, Irpex, Penicillium, Sclerotium,* and *Torulopsis*. Especially contemplated are proteases derived from *Aspergillus niger* (see, e.g., Koaze et. al., 1964, *Agr. Biol. Chem. Japan* 28: 216), *Aspergillus saitoi* (see, e.g., Yoshida, 1954, *J. Agr. Chem. Soc. Japan* 28: 66), *Aspergillus awamori* (Hayashida et al., 1977, *Agric. Biol. Chem.* 42: 927-933, *Aspergillus aculeatus* (WO 95/02044), or *Aspergillus oryzae;* and acidic proteases from *Mucor pusillus* or *Mucor miehei*.

Bacterial proteases, which are not acidic proteases, include the commercially available products ALCALASE™ and NEUTRASE™ (available from Novozymes A/S). Other proteases include GC106 from Genencor International, Inc., USA and NOVOZYM™ 50006 from Novozymes A/S.

Preferably, the protease is an aspartic acid protease, as described, for example, in *Handbook of Proteolytic Enzymes*, Edited by A. J. Barrett, N. D. Rawlings and J. F. Woessner, Academic Press, San Diego, 1998, Chapter 270). Suitable examples of aspartic acid protease include, e.g., those disclosed by Berka et al., 1990, Gene 96: 313; Berka et al., 1993, Gene 125: 195-198; and Gomi et al., 1993, *Biosci. Biotech. Biochem*. 57: 1095-1100.

Peroxidases

Other compounds possessing peroxidase activity may be any peroxidase (EC 1.11.1.7), or any fragment having peroxidase activity derived therefrom, exhibiting peroxidase activity.

Preferably, the peroxidase is produced by plants (e.g., horseradish or soybean peroxidase) or microorganisms such as fungi or bacteria.

Some preferred fungi include strains belonging to the subdivision *Deuteromycotina*, class Hyphomycetes, e.g., *Fusarium, Humicola, Tricoderma, Myrothecium, Verticillum, Arthromyces, Caldariomyces, Ulocladium, Embellisia, Cladosporium,* or *Dreschlera*, in particular, *Fusarium oxysporum* (DSM 2672), *Humicola insolens, Trichoderma reesei, Myrothecium verrucaria* (IFO 6113), *Verticillum alboatrum, Verticillum dahlie, Arthromyces ramosus* (FERM P-7754), *Caldariomyces fumago, Ulocladium chartarum, Embellisia alli,* or *Dreschlera halodes*.

Other preferred fungi include strains belonging to the subdivision *Basidiomycotina*, class Basidiomycetes, e.g., *Coprinus, Phanerochaete, Coriolus,* or *Trametes*, in particular *Coprinus cinereus f. microsporus* (IFO 8371), *Coprinus macrorhizus, Phanerochaete chrysosporium* (e.g. NA-12), or *Trametes* (previously called *Polyporus*), e.g., *T. versicolor* (e.g., PR4 28-A).

Further preferred fungi include strains belonging to the subdivision *Zygomycotina*, class Mycoraceae, e.g., *Rhizopus* or *Mucor*, in particular *Mucor hiemalis*.

Some preferred bacteria include strains of the order Actinomycetales, e.g. *Streptomyces spheroides* (ATTC 23965), *Streptomyces thermoviolaceus* (IFO 12382), or *Streptoverticillum verticillium* ssp. *verticillium*.

Other preferred bacteria include *Rhodobacter sphaeroides, Rhodomonas palustri, Streptococcus lactis, Pseudomonas purrocinia* (ATCC 15958), *Pseudomonas fluorescens* (NRRL B-11), and *Bacillus* strains, e.g., *Bacillus pumilus* (ATCC 12905) and *Bacillus stearothermophilus*.

Further preferred bacteria include strains belonging to *Myxococcus*, e.g., *M. virescens*.

The peroxidase may also be one which is produced by a method comprising cultivating a host cell transformed with a recombinant DNA vector which carries a DNA sequence encoding the peroxidase as well as DNA sequences for expression of the DNA sequence encoding the peroxidase, in a culture medium under conditions permitting the expression of the peroxidase and recovering the peroxidase from the culture.

In a preferred aspect, a recombinantly produced peroxidase is a peroxidase derived from a *Coprinus* sp., in particular *C. macrorhizus* or *C. cinereus* according to WO 92/16634.

In the present invention, compounds possessing peroxidase activity comprise peroxidase enzymes and peroxidase active fragments derived from cytochromes, hemoglobin, or peroxidase enzymes.

One peroxidase unit (POXU) is the amount of enzyme which under the following conditions catalyzes the conversion of 1 μmole hydrogen peroxide per minute at 30° C. in 0.1 M phosphate buffer pH 7.0, 0.88 mM hydrogen peroxide, and 1.67 mM 2,2'-azino-bis(3-ethylbenzothiazoline-6-sulfonate) (ABTS). The reaction is followed for 60 seconds (15 seconds after mixing) by the change in absorbance at 418 nm, which should be in the range of 0.15 to 0.30. For calculation of activity, an absorption coefficient of oxidized ABTS of 36 mM-1 cm-1 and a stoichiometry of one μmole $H_2O_2$ converted per two μmole ABTS oxidized are used.

Laccases

In the present invention, laccases and laccase related enzymes comprise any laccase enzyme classified as EC 1.10.3.2, any catechol oxidase enzyme classified as EC 1.10.3.1, any bilirubin oxidase enzyme classified as EC 1.3.3.5, or any monophenol monooxygenase enzyme classified as EC 1.14.18.1.

The above-mentioned enzymes may be microbial, i.e., obtained from bacteria or fungi (including filamentous fungi and yeasts), or they may be derived from plants.

Suitable examples from fungi include a laccase obtained from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizooctonia*, e.g., *R. solani*, *Coprinus*, e.g., *C. cinereus*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Pycnoporus*, e.g., *P. cinnabarinus*, *Phlebia*, e.g., *P. radita* (WO 92/01046), or *Coriolus*, e.g., *C. hirsutus* (JP 2-238885).

Suitable examples from bacteria include a laccase obtained from a strain of *Bacillus*.

A laccase obtained from *Coprinus*, *Myceliophthora*, *Polyporus*, *Pycnoporus*, *Scytalidium* or *Rhizoctonia* is preferred; in particular a laccase obtained from *Coprinus cinereus*, *Myceliophthora thermophila*, *Polyporus pinsitus*, *Pycnoporus cinnabarinus*, *Scytalidium thermophilum*, or *Rhizoctonia solani*.

Commercially available laccases are NS51001 (a *Polyporus pinsitius* laccase, available from Novozymes A/S, Denmark) and NS51002 (a *Myceliopthora thermophila* laccase, available from Novozymes A/S, Denmark).

The laccase or the laccase related enzyme may also be one which is produced by a method comprising cultivating a host cell transformed with a recombinant DNA vector which carries a DNA sequence encoding the laccase as well as DNA sequences for expression of the DNA sequence encoding the laccase, in a culture medium under conditions permitting the expression of the laccase enzyme, and recovering the laccase from the culture.

Laccase activity (LACU) is determined from the oxidation of syringaldazine under aerobic conditions at pH 5.5. The violet color produced is measured at 530 nm. The analytical conditions are 19 mM syringaldazine, 23 mM acetate buffer, pH 5.5, 30° C., 1 minute reaction time. One laccase unit (LACU) is the amount of enzyme that catalyses the conversion of 1.0 μmole syringaldazine per minute under the above conditions.

Laccase activity (LAMU) is determined from the oxidation of syringaldazine under aerobic conditions at pH 7.5. The violet color produced is photometered at 530 nm. The analytical conditions are 19 mM syringaldazine, 23 mM Tris/maleate pH 7.5, 30° C., 1 minute reaction time. One laccase unit (LAMU) is the amount of enzyme that catalyses the conversion of 1.0 μmole syringaldazine per minute under the above conditions.

The polypeptides having cellulolytic enhancing activity may be used in conjunction with the above-noted enzymes and/or cellulolytic proteins to further degrade the cellulose component of the biomass substrate, (see, for example, Brigham et al., 1995, in *Handbook on Bioethanol* (Charles E. Wyman, editor), pp. 119-141, Taylor & Francis, Washington D.C.; Lee, 1997, *Journal of Biotechnology* 56: 1-24).

The optimum amounts of a polypeptide having cellulolytic enhancing activity and of cellulolytic proteins depends on several factors including, but not limited to, the mixture of component cellulolytic proteins, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In a preferred aspect, an effective amount of polypeptide(s) having cellulolytic enhancing activity to cellulosic material is about 0.01 to about 2.0 mg, preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulosic material.

In another preferred aspect, an effective amount of cellulolytic protein(s) to cellulosic material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In a preferred aspect, an effective amount of polypeptide(s) having cellulolytic enhancing activity to cellulolytic protein(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic protein(s).

Detergent Compositions

The polypeptides having cellulolytic enhancing activity may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide having cellulolytic enhancing activity as described herein. The detergent additive as well as the detergent composition may comprise one or more enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OXP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. sub-* *tilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipex™, and Lipolase Ultra™ (Novozymes A/S).

Amylases: Suitable amylases (alpha and/or beta) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), and Rapidase™ and Purastar™ (from Genencor International Inc.).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

A detergent composition of the present invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a polypeptide having cellulolytic enhancing activity may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A polypeptide of the invention having cellulolytic enhancing activity may also be incorporated in the detergent formulations disclosed in WO 97/07202, which is hereby incorporated by reference.

The present invention is further described by the following examples which should not be construed as limiting the scope of the invention.

EXAMPLES

Materials

Chemicals used as buffers and substrates were commercial products of at least reagent grade.

Strains

*Trichoderma reesei* RutC30 (ATCC 56765; Montenecourt and Eveleigh, 1979, *Adv. Chem. Ser.* 181: 289-301) was used as the source of a *Trichoderma reesei* gene encoding a Family 61 polypeptide having cellulolytic enhancing activity. *Aspergillus oryzae* JaL250 strain (WO 99/61651) was used for expression of the *Trichoderm reesei* Family 61 polypeptide having cellulolytic enhancing activity.

Media

PDA plates were composed per liter of 39 grams of potato dextrose agar.

MDU2BP medium was composed per liter of 45 g of maltose, 1 g of $MgSO_4.7H_2O$, 1 g of NaCl, 2 g of $K_2SO_4$, 12 g of $KH_2PO_4$, 7 g of yeast extract, 2 g of urea, and 0.5 ml of AMG trace metals solution, pH to 5.0.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

LB plates were composed per liter of 10 g of tryptone, 5 g of yeast extract, 5 g of sodium chloride, and 15 g of Bacto Agar.

SOC medium was composed of 2% tryptone, 0.5% yeast extract, 10 mM NaCl, 2.5 mM KCl, 10 mM $MgCl_2$, and 10 mM $MgSO_4$, and filter-sterilized glucose to 20 mM added after autoclaving.

Example 1

Fermentation and Mycelial Tissue

*Trichoderma reesei* strain RutC30 was cultivated in a pilot scale fermentation tank in growth medium containing a complex carbon source. The carbon sources included glucose, cellulose, or pre-treated and washed corn stover. Fungal mycelium was collected from a one-liter sample, and immediately frozen in liquid $N_2$ and stored at −80° C.

Pretreated corn stover (PCS) was obtained from the U.S. Department of Energy National Renewable Energy Laboratory (NREL). The water-insoluble solids in PCS are 56.5% cellulose, 4.6% hemicellulose, and 28.4% lignin. Pretreatment conditions were corn stover, 1.4% (wt/vol) sulfuric acid, 165° C., 107 psi, for 8 minutes. Prior to assay, PCS was washed with a large volume of distilled deionized water on a glass filter. PCS was then milled using a coffee grinder to reduce particle size, and washed further with water on a 22 μm Millipore filter (6P Express Membrane, Stericup, Millipore, Billerica, Mass.). The washed PCS was resuspended in deionized water to make a 20 mg/ml suspension, and stored at 4° C.

Example 2

*Trichoderma reesei* Directional cDNA Library Construction

Total RNA was prepared from the *Trichoderma reesei* mycelial samples described in Example 1 by extraction with guanidinium thiocyanate followed by ultracentrifugation through a 5.7 M CsCl cushion (Chirgwin et al., 1979, *Biochemistry* 18: 5294-5299) using the following modifications. The frozen mycelia were ground in liquid $N_2$ to a fine powder with a mortar and a pestle, followed by grinding in a precooled coffee mill, and immediately suspended in 5 volumes of RNA extraction buffer (4 M guanidinium thiocyanate, 0.5% sodium laurylsarcosine, 25 mM sodium citrate pH 7.0, 0.1 M β-mercaptoethanol). The mixture was stirred for 30 minutes at room temperature and centrifuged (20 minutes at 12,000×g) to pellet the cell debris. The supernatant was collected, carefully layered onto a 5.7 M CsCl cushion (5.7 M CsCl, 10 mM EDTA, pH 7.5, 0.1% diethylpyrocarbonate (DEPC); autoclaved prior to use) using 26.5 ml of supernatant per 12.0 ml of CsCl cushion, and centrifuged to obtain the total RNA (Beckman SW 28 rotor, 25,000 rpm, room temperature, 24 hours). After centrifugation the supernatant was carefully removed and the bottom of the tube containing the RNA pellet was cut off and rinsed with 70% ethanol. The total RNA pellet was transferred to an Eppendorf tube, suspended in 500 μl of TE (10 mM Tris-0.1 mM EDTA), pH 7.6 (if difficult, heated occasionally for 5 minutes at 65° C.), phenol extracted, and precipitated with ethanol for 12 hours at −20° C. (2.5 volumes of ethanol, 0.1 volume of 3M sodium acetate pH 5.2). The RNA was collected by centrifugation (30 minutes at 12,000×g), washed in 70% ethanol, and resuspended in a minimum volume of DEPC-treated water. The total RNA concentration was determined by measuring the absorbance at 260 nm.

Poly(A)$^+$ RNA was isolated by oligo(dT)-cellulose affinity chromatography (Aviv & Leder, 1972, *Proceedings of the National Academy of Sciences USA* 69: 1408-1412). A total of 0.2 g of oligo(dT) cellulose (Boehringer Mannheim, Indianapolis, Ind.) was pre-swollen in 10 ml of 1× of column loading buffer (20 mM Tris-Cl, pH 7.6, 0.5 M NaCl, 1 mM EDTA, 0.1% SDS), loaded onto a DEPC-treated, plugged plastic column (Poly Prep Chromatography Column, Bio-Rad, Hercules, Calif.), and equilibrated with 20 ml of 1× loading buffer. The total RNA (1-2 mg) was heated at 65° C. for 8 minutes, quenched on ice for 5 minutes, and after addition of 1 volume of 2× column loading buffer loaded onto the column. The eluate was collected and reloaded 2-3 times by heating the sample as above and quenching on ice prior to each loading. The oligo(dT) column was washed with 10 volumes of 1×0 loading buffer, then with 3 volumes of medium salt buffer (20 mM Tris-Cl, pH 7.6, 0.1 M NaCl, 1 mM EDTA, 0.1% SDS), followed by elution of the poly(A)$^+$ RNA with 3 volumes of elution buffer (10 mM Tris-Cl pH 7.6, 1 mM EDTA, 0.05% SDS) preheated to 65° C., by collecting 500 μl fractions. The absorbance at 260 nm was read for each collected fraction, and the mRNA containing fractions were pooled and ethanol precipitated at −20° C. for 12 hours. The poly(A)$^+$ RNA was collected by centrifugation, resuspended in DEPC-treated water, and stored in 5-10 μg aliquots at −80° C.

Double-stranded Eco RI-Not I-directional cDNA was synthesized from 5 μg of *Trichoderma reesei* RutC30 poly(A)$^+$ RNA by the RNase H method (Gubler and Hoffman 1983, *Gene* 25: 263-270; Sambrook et al., 1989, *Molecular Cloning, a Laboratory Manual.* Cold Spring Harbor Laboratory Press, Cold Spring Harbor, N.Y.) using a hair-pin modification. The poly(A)$^+$ RNA (5 μg in 5 μl of DEPC-treated water) was heated at 70° C. for 8 minutes in a pre-siliconized, RNase-free Eppendorf tube, quenched on ice, and combined in a final volume of 50 μl with reverse transcriptase buffer (50 mM Tris-Cl pH 8.3, 75 mM KCl, 3 mM $MgCl_2$, 10 mM DTT) containing 1 mM of dATP, dGTP and dTTP, 0.5 mM of 5-methyl-dCTP, 40 units of human placental ribonuclease inhibitor (Promega, Madison, Wis.), 4.81 μg of oligo(dT)$_{18}$-Not I primer, and 1000 units of SuperScript II RNase H—reverse transcriptase (Life Technologies, Inc., Rockville, Md.). First-strand cDNA was synthesized by incubating the reaction mixture at 45° C. for 1 hour. After synthesis, the mRNA: cDNA hybrid mixture was gel filtrated through a MicroSpin S-400 HR spin column (Amersham Biosciences, Piscataway, N.J.) according to the manufacturer's instructions.

After gel filtration, the hybrids were diluted in 250 μl of second strand buffer (20 mM Tris-Cl pH 7.4, 90 mM KCl, 4.6 mM $MgCl_2$, 10 mM $(NH_4)_2SO_4$, 0.16 mM NAD$^+$) containing 200 μM of each dNTP, 60 units of *E. coli* DNA polymerase I (Amersham Biosciences, Piscataway, N.J.), 5.25 units of RNase H, and 15 units of *E. coli* DNA ligase (New England Biolabs, Inc., Beverly, Mass.). Second strand cDNA synthesis was performed by incubating the reaction tube at 16° C. for 2 hours, and an additional 15 minutes at 25° C. The reaction was stopped by addition of EDTA to 20 mM final concentration followed by phenol and chloroform extractions.

The double-stranded cDNA was ethanol precipitated at −20° C. for 12 hours by addition of 2 volumes of 96% ethanol and 0.2 volume of 10 M ammonium acetate, recovered by centrifugation, washed in 70% ethanol, dried (SpeedVac), and resuspended in 30 μl of Mung bean nuclease buffer (30 mM sodium acetate pH 4.6, 300 mM NaCl, 1 mM $ZnSO_4$, 0.35 mM dithiothreitol, 2% glycerol) containing 25 units of Mung bean nuclease. The single-stranded hair-pin DNA was clipped by incubating the reaction at 30° C. for 30 minutes, followed by addition of 70 μl of 10 mM Tris-Cl, pH 7.5, 1 mM EDTA, phenol extraction, and ethanol precipitation with 2 volumes of 96% ethanol and 0.1 volume 3 M sodium acetate pH 5.2 on ice for 30 minutes.

The double-stranded cDNAs were recovered by centrifugation (30,000×g for 30 minutes), and blunt-ended with T4 DNA polymerase in 30 μl of T4 DNA polymerase buffer (20 mM Tris-acetate, pH 7.9, 10 mM magnesium acetate, 50 mM potassium acetate, 1 mM dithiothreitol) containing 0.5 mM of each dNTP, and 5 units of T4 DNA polymerase by incubating the reaction mixture at 16° C. for 1 hour. The reaction was stopped by addition of EDTA to 20 mM final concentration, followed by phenol and chloroform extractions and ethanol precipitation for 12 hours at −20° C. by adding 2 volumes of 96% ethanol and 0.1 volume of 3 M sodium acetate pH 5.2.

After the fill-in reaction, cDNA was recovered by centrifugation as above, washed in 70% ethanol, and the DNA pellet was dried in a SpeedVac. The cDNA pellet was resuspended in 25 μl of ligation buffer (30 mM Tris-Cl, pH 7.8, 10 mM $MgCl_2$, 10 mM dithiothreitol, 0.5 mM ATP) containing 2 μg of Eco RI adaptors (0.2 μg/μl, Amersham Biosciences, Piscataway, N.J.) and 20 units of T4 ligase (Roche Molecular Biochemicals, Indianapolis, Ind.) by incubating the reaction mix at 16° C. for 12 hours. The reaction was stopped by heating at 65° C. for 20 minutes, and then placed on ice for 5 minutes. The adapted cDNA was digested with Not I by addition of 20 μl of autoclaved water, 5 μl of 10× Not I restriction enzyme buffer, and 50 units of Not I, followed by incubation for 3 hours at 37° C. The reaction was stopped by heating the sample at 65° C. for 15 minutes. The cDNAs were size-fractionated by agarose gel electrophoresis on a 0.8% SeaPlaque GTG low melting temperature agarose gel (FMC, Rockland, Me.) in 44 mM Tris Base, 44 mM boric acid, 0.5 mM EDTA (TBE) buffer (in autoclaved water) to separate unligated adaptors and small cDNAs. The gel was run for 12 hours at 15 V, and the cDNA was size-selected with a cut-off at 0.7 kb by cutting out the lower part of the agarose gel. Then a 1.5% agarose gel was poured in front of the cDNA-containing gel, and the double-stranded cDNAs were concentrated by running the gel backwards until it appeared as a compressed band on the gel. The cDNA-containing gel piece was cut out from the gel and the cDNA was extracted from the gel using a GFX Gel Band Purification Kit (Amersham, Arlington Heights, Ill.) as follows. The trimmed gel slice was weighed in a 2 ml nuclease-free microcentrifuge tube (ISC BioExpress, Kaysville, Utah). Then 10 ml of Capture Buffer (Amersham, Arlington Heights, Ill.) was added for each 10 mg of gel slice. The gel slice was dissolved by incubation at 60° C. for 10 minutes, until the agarose was completely solubilized, and the sample was then pelleted by a brief centrifugation (2 minutes at 8,000×g). The melted sample was transferred to a GFX spin column placed in a collection tube, incubated at 25° C. for 1 minute, and then centrifuged at full speed (15,000×g) in a microcentrifuge for 30 seconds. The flow-through was discarded, and the column was washed with 500 µl of wash buffer (GFX Gel Band Purification Kit, Amersham, Arlington Heights, Ill.) followed by centrifugation at full speed for 30 seconds. The collection tube was discarded, and the column was placed in a 1.5 ml Eppendorf tube, followed by elution of the cDNA by addition of 50 µl of TE pH 7.5 to the center of the column, incubation at 25° C. for 1 minute, and finally by centrifugation for 1 minute at maximum speed (15,000×g). The eluted cDNA was stored at −20° C. until library construction.

A plasmid DNA preparation for a Eco RI-Not I insert-containing pYES2.0 cDNA clone was purified using a QIAGEN Tip-100 according to the manufacturer's instructions (QIAGEN, Valencia, Calif.). A total of 10 µg of purified plasmid DNA was digested to completion with Not I and Eco RI in a total volume of 60 µl by addition of 6 µl of 10× NEBuffer for Eco RI (New England Biolabs, Beverly, Mass.), 40 units of Not I, and 20 units of Eco RI followed by incubation for 6 hours at 37° C. The reaction was stopped by heating the sample at 65° C. for 20 minutes. The digested plasmid DNA was extracted once with phenol-chloroform, then with chloroform, followed by ethanol precipitation for 12 hours at −20° C. by adding 2 volumes of 96% ethanol and 0.1 volume of 3 M sodium acetate pH 5.2. The precipitated DNA was resuspended in 25 µl of TE pH 7.5, loaded onto a 0.8% SeaKem agarose gel in TBE buffer, and run for 3 hours at 60 V. The digested vector was cut out from the gel, and the DNA was extracted from the gel using a GFX Gel Band Purification Kit according to the manufacturer's instructions. After measuring the DNA concentration by absorbance at 260 nm, the eluted vector was stored at −20° C. until library construction.

To establish the optimal ligation conditions for the cDNA library, four test ligations were performed in 10 µl of ligation buffer (30 mM Tris-Cl pH 7.8, 10 mM MgCl$_2$, 10 mM DTT, 0.5 mM ATP) containing 7 µl of double-stranded cDNA (corresponding to approximately ¹⁄₁₀ of the total volume in the cDNA sample), 2 units of T4 ligase, and 25 ng, 50 ng and 75 ng of Eco RI-Not I cleaved pYES2.0 vector (Invitrogen, Carlsbad, Calif.), respectively. The vector background control ligation reaction contained 75 ng of Eco RI-Not I cleaved pYES.0 vector without cDNA. The ligation reactions were performed by incubation at 16° C. for 12 hours, heated at 65° C. for 20 minutes, and then 10 µl of autoclaved water was added to each tube. One µl of the ligation mixtures was electroporated (200 W. 2.5 kV, 25 mF) to 40 µl of electrocompetent *E. coli* DH10B cells (Life Technologies, Gaithersburg, Md.). After addition of 1 ml of SOC medium (Birren et al., 1998. *Genome Analysis, Vol. 2. Detecting Genes.* Cold Spring Harbor Laboratory Press, Cold Spring Harbor, N.Y.) to each transformation mix, the cells were grown at 37° C. for 1 hour.

Then 50 µl and 5 µl from each electroporation were plated on LB plates supplemented with ampicillin at 100 µg per ml and grown at 37° C. for 12 hours. Using the optimal conditions, a *Trichoderma reesei* RutC30 cDNA library containing 1-2.5× 10$^7$ independent colony forming units was established in *E. coli*, with a vector background of ca. 1%. The cDNA library was stored as (1) individual pools (25,000 c.f.u./pool) in 20% glycerol at −80° C.; (2) cell pellets of the same pools at −20° C.; (3) QIAGEN Tip 100 purified plasmid DNA from individual pools at −20° C.; and (4) directional, double-stranded cDNA at −20° C.

Example 3

*Trichoderma reesei* EST Template Preparation

Plasmid DNAs from individual *E. coli* colonies from the cDNA libraries described in Example 2 were purified using a 96-well manifold plasmid preparation system (QIAGEN, Valencia, Calif.) according to instructions supplied by the manufacturer.

Example 4

Analysis of DNA Sequence Data of cDNA Clones

Base calling, quality value assignment, and vector trimming were performed with the assistance of PHRED/PHRAP software (University of Washington, Seattle, Wash.). Sequence homology analysis of the assembled EST sequences against the PIR database was performed with the Blastx program (Altschul et. al.,1990, *J. Mol. Biol.* 215:403-410) on a 32-node Linux cluster (Paracel, Inc., Pasadena, Calif.) using the BLOSUM 62 matrix (Henikoff, 1992, *Proc. Natl. Acad. Sci. USA* 89:10915-10919).

Example 5

Identification of a cDNA Clone Encoding a Family 61 Polypeptide Having Cellulolytic Enhancing Activity (GH61B)

A cDNA clone encoding a Family 61 polypeptide having cellulolytic enhancing activity (GH61B) was initially identified by the similarity of its translated product to other known Family 61 polypeptides present in public databases. Specifically, this analysis indicated that the predicted polypeptide was 50% identical at the protein level to the core domain of endoglucanase IV of *Trichoderma reesei*, a known member of Family 61 (Saloheimo et al., 1997, *Eur. J. Biochem.* 249: 584-591). After this initial identification, the EST clone was retrieved from it original frozen stock plate and streaked onto LB plates supplemented with 100 µg of ampicillin per ml. The plates were incubated overnight at 37° C. and the next day a single colony from each plate was used to inoculate 3 ml of LB supplemented with 100 µg of ampicillin per ml. The liquid cultures were incubated overnight at 37° C. and plasmid DNA was prepared with a BioRobot 9600 (QIAGEN Inc., Valencia, Calif.). Plasmid DNA from each EST clone was sequenced again with Big-Dye™ terminator chemistry (Applied Biosystems, Inc., Foster City, Calif.), using the M13 forward and a Poly-T primer shown below to sequence the 3' end of the clone.

```
                                                    (SEQ ID NO: 3)
         5'-TTTTTTTTTTTTTTTTTTTTTTVN-3'
``` where V=G, A, or C and N=G, A, C, or T

One clone, *Trichoderma reesei* EST Tr3337 designated pTr3337, was selected for nucleotide sequence analysis.

Example 6

Characterization of a *Trichoderma reesei* cDNA Clone Encoding a Polypeptide Having Cellulolytic Enhancing Activity Three new primers shown below were designed to extend the sequence information from EST pTr3337 (FIG. 2).

```
                                (SEQ ID NO: 4)
         5'-TGTCCATGGCCGAGA-3'

(SEQ ID NO: 5)
         5'-ATACTGGTCACTTCCCCAA-3'

(SEQ ID NO: 6)
         5'-GCGCTGGGTCAAGATT-3'
```

DNA sequencing was performed on a Perkin-Elmer Biosystems Model 377 XL Automated DNA Sequencer using dye-terminator chemistry (Giesecke et al., 1992, *Journal of Virology Methods* 38: 47-60). The 1.17 kb cDNA fragment was sequenced to a Phred quality value of 36.

The nucleotide sequence (SEQ ID NO: 1) and deduced amino acid sequence (SEQ ID NO: 2) of the coding region of the *Trichoderma reesei* GH61B cDNA clone are shown in FIG. 1. The coding sequence is 750 bp including the stop codon. The encoded predicted protein is 249 amino acids. The coding region is 56.8% G+C. Using the SignalP program (Nielsen et al., 1997, *Protein Engineering* 10: 1-6), a signal peptide of 19 residues was predicted. The predicted mature protein contains 230 amino acids with a molecular mass of 25.1 kDa and isoelectric point (pI) of 7.36.

Analysis of the mature peptide with the Interproscan program (Zdobnov and Apweiler, 2001, *Bioinformatics* 17: 847-8) showed that the gene encoded by clone Tr3337 contained the sequence signature of the glycosyl hydrolase Family 61 proteins. This sequence signature known as the Pfam pattern PF03443 (Bateman et. al., 2004, *Nucleic Acids Research* 32: 138-141) is located from residue 20 to 241 confirming that clone Tr3337 encodes a *Trichoderma reseei* Family 61 gene.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Trichoderma reesei* gene encoding the GH61B mature polypeptide having cellulolytic enhancing activity shared 100% and 62% identity (excluding gaps) to the deduced amino acid sequences of two glycosyl hydrolase Family 61 proteins from *Trichoderma reesei* (GeneSeP ADH34517) and *Chaetomium globosum* (UniProt Q2GPR1), respectively.

An *E. coli* strain containing plasmid pTr3337 was deposited with the Agricultural Research Service Patent Culture Collection, Northern Regional Research Center, 1815 University Street, Peoria, Ill., 61604, as NRRL B-30878, with a deposit date of Sep. 20, 2005.

Example 7

Construction of an *Aspergillus oryzae* Expression Vector for the *Trichoderma reesei* Family GH61B Gene Two synthetic oligonucleotide primers shown below were designed to PCR amplify the *Trichoderma reesei* Family GH61B gene from the cDNA clone. An InFusion Cloning Kit (BD Biosciences, Palo Alto, Calif.) was used to clone the fragment directly into the expression vector, pAILo2 (WO 2005/074647), without the need for restriction digests and ligation.

```
Forward primer:
                                          (SEQ ID NO: 7)
    5'-ACTGGATTTACCATGAAGTCCTGCGCCATTCTTGC-3'

Reverse primer:
                                          (SEQ ID NO: 8)
    5'-AGTCACCTCTAGTTAGCCTTGCCACAGGGCTGG-3'
```

Bold letters represent coding sequence. The remaining sequence is homologous to the insertion sites of pAILo2.

Fifty picomoles of each of the primers above were used in a PCR reaction containing 100 ng of *Trichoderma reesei* cDNA clone (prepared as described in Example 5), 1× Pfx Amplification Buffer (Invitrogen, Carlsbad, Calif.), 6 µl of 10 mM blend of dATP, dTTP, dGTP, and dCTP, 2.5 units of Platinum Pfx DNA Polymerase (Invitrogen, Carlsbad, Calif.), 1 µl of 50 mM $MgSO_4$, and 5 µl of 10× pCRx Enhancer Solution (Invitrogen, Carlsbad, Calif.) in a final volume of 50 µl. The amplification conditions were one cycle at 94° C. for 2 minutes; and 30 cycles each at 94° C. for 15 seconds, 55° C. for 30 seconds, and 68° C. for 3 minutes. The heat block then went to a 4° C. soak cycle.

The reaction products were isolated on a 1.0% agarose gel using 40 mM Tris base-20 mM sodium acetate-1 mM disodium EDTA (TAE) buffer where a 3 kb product band was excised from the gel and purified using a QIAquick Gel Extraction Kit (QIAGEN Inc., Valencia, Calif.) according to the manufacturer's instructions.

Figure 3:
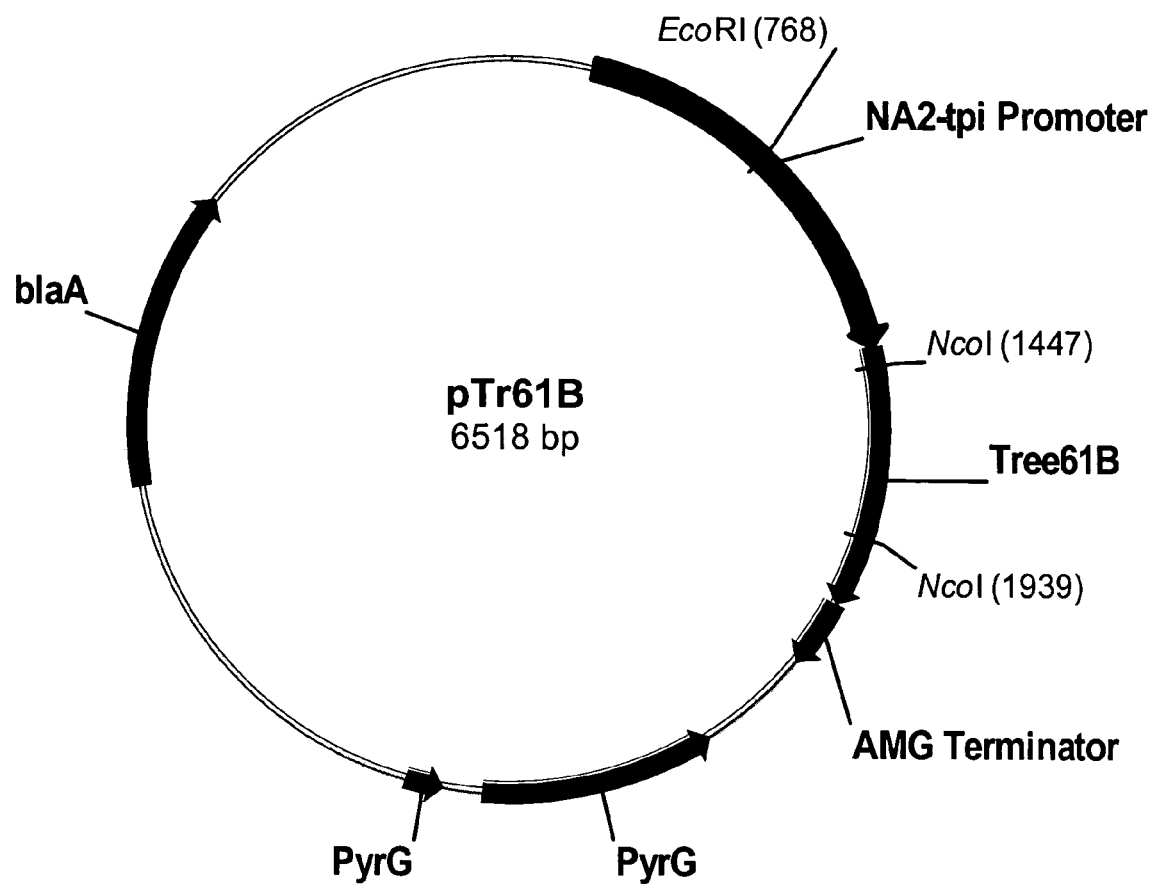
FIG. 3 shows a restriction map of pTr61B.

The fragment was then cloned into pAILo2 using an InFusion Cloning Kit. The vector was digested with Nco I and Pac I (using conditions specified by the manufacturer). The fragment was purified by gel electrophoresis and QIAquick gel purification. The gene fragment and the digested vector were combined together in a reaction resulting in the expression plasmid pTr61B (FIG. 3) in which transcription of the Family GH61B gene was under the control of the NA2-tpi promoter (a hybrid of the promoters from the genes for *Aspergillus niger* neutral alpha-amylase and *Aspergillus oryzae* triose phosphate isomerase). The recombination reaction (20 µl) was composed of 1× InFusion Buffer (BD Biosciences, Palo Alto, Calif.), 1× BSA (BD Biosciences, Palo Alto, Calif.), 1 µl of InFusion enzyme (diluted 1:10) (BD Biosciences, Palo Alto, Calif.), 100 ng of pAILo2 digested with Nco I and Pac I, and 100 ng of the *Trichoderma reesei* GH61B purified PCR product. The reaction was incubated at room temperature for 30 minutes. One µl of the reaction was used to transform *E. coli* XL10 Solopac Gold cells (Stratagene, La Jolla, Calif.). An *E. coli* transformant containing pTr61B (GH61B gene)

was identified by restriction enzyme digestion and plasmid DNA was prepared using a QIAGEN BioRobot 9600.

Example 8

Expression of the *Trichoderma reesei* cDNA Encoding Family GH61B Polypeptides Having Cellulolytic Enhancing Activity in *Aspergillus oryzae* JaL250

*Aspergillus oryzae* JaL250 protoplasts were prepared according to the method of Christensen et al., 1988, *Bio/Technology* 6: 1419-1422. Five μg of pTr61B (as well as pAILo2 as a vector control) was used to transform *Aspergillus oryzae* JaL250.

The transformation of *Aspergillus oryzae* JaL250 with pTr61B (GH61B gene) yielded about 70 transformants. Ten transformants were isolated to individual PDA plates.

Confluent PDA plates of all transformants were washed with 5 ml of 0.01% Tween 80 and inoculated separately into 25 ml of MDU2BP medium in 125 ml glass shake flasks and incubated at 34° C., 200 rpm. Five days after incubation, 5 μl of supernatant from each culture was analyzed using 8-16% Tris-Glycine SDS-PAGE gels (Invitrogen, Carlsbad, Calif.) according to the manufacturer's instructions. SDS-PAGE profiles of the cultures showed that several transformants had a new major band of approximately 25 kDa.

A confluent plate of one transformant (grown on PDA) was washed with 10 ml of 0.01% Tween 20 and inoculated into a 2 liter Fernbach containing 500 ml of MDU2BP medium to generate broth for characterization of the enzyme. The flask was harvested on day 5 and filtered using a 0.22 μm GP Express plus Membrane (Millipore, Bedford, Mass.).

Example 9

Effect of *Trichoderma reesei* GH61B on Hydrolysis of Pretreated Corn Stover by *Trichoderma reesei* Fermentation Broth Expressing *Aspergillus oryzae* Beta-Glucosidase

*Trichoderma reesei* GH61B (recombinantly produced in *Aspergillus oryzae* as described in Example 8) was desalted and exchanged to 50 mM sodium acetate pH 5.0 using a Centricon Plus-20 centrifugal filter with a Biomax-5 membrane (5000 NMWL; Millipore, Bedford, Mass.) before hydrolysis experiments. Cell-free *Trichoderma reesei* fermentation broth expressing *Aspergillus oryzae* beta-glucosidase, prepared as described in WO 2005/074647, was used in hydrolysis experiments without desalting or buffer exchange.

Enzyme dilutions were prepared fresh before each experiment from stock enzyme solutions, which were stored at -20° C.

Reducing sugars (RS) were determined using a p-hydroxybenzoic acid hydrazide (PHBAH) assay (Lever, M., 1972, A new reaction for colorimetric determination of carbohydrates, *Anal. Biochem.* 47: 273-279), which was modified and adapted to a 96-well microplate format.

A 90 μl aliquot of the diluted sample was placed into each well of a 96-well conical-bottomed microplate (Corning Inc., Acton, Mass., Costar, clear polycarbonate). The assay was started by adding 60 μl of 1.25% PHBAH in 2% sodium hydroxide to each well. The uncovered plate was heated on a custom-made heating block for 10 minutes at 95° C. After the microplate was cooled to room temperature, 35 μl of deionized water was added to each well. A 100 μl aliquot was removed from each well and transferred to a flat-bottomed 96-well plate (Corning Inc., Acton, Mass., Costar, medium binding polystyrene). The absorbance at 410 nm ($A_{410}$) was measured using a SpectraMAX Microplate Reader (Molecular Devices, Sunnyvale, Calif.). The $A_{410}$ value was translated into glucose equivalents using a standard curve.

The standard curve was obtained with six glucose standards (0.005, 0.010, 0.025, 0.050, 0.075, and 0.100 mg/ml), which were treated similarly to the samples. Glucose standards were prepared by diluting 10 mg/ml stock glucose solution with deionized water.

The degree of cellulose conversion to reducing sugar (conversion, %) was calculated using the following equation:

$$Conversion_{(\%)} = RS_{(mg/ml)} * 100 * 162 / (Cellulose_{(mg/ml)} * 180)$$
$$= RS_{(mg/ml)} * 100 / (Cellulose_{(mg/ml)} * 1.111)$$

In this equation, RS is the concentration of reducing sugar in solution measured in glucose equivalents (mg/ml), and the factor 1.111 reflects the weight gain in converting cellulose to glucose.

Hydrolysis of milled PCS (1% w/v on a dry weight basis) by the cell-free *Trichoderma reesei* fermentation broth expressing *Aspergillus oryzae* beta-glucosidase was carried out in Deepwell Plates 96 (1.2 ml, Brinkmann, Westbury, N.Y.) capped with Deepwell Mats 96 (Brinkmann, Westbury, N.Y.). All reactions with the initial volume of 1 ml were run in 50 mM sodium acetate pH 5.0 with intermittent stirring at 50° C.

Time-course reactions containing the *Trichoderma reesei* fermentation broth at 2.5 mg per g of PCS were supplemented with *Trichoderma reesei* GH61B (recombinantly produced in *Aspergillus oryzae* as described herein) at 0.625 mg per g of PCS (25% of cellulase protein loading), and the results were compared with non-supplemented *Trichoderma reesei* broth at 2.5 and 3.125 mg per g of PCS or compared with *Trichoderma reesei* GH61B protein alone at 2.5 mg per g of PCS.

Protein loading reactions containing the *Trichoderma reesei* fermentation broth at 2.5 mg per g of PCS were supplemented with *Trichoderma reesei* GH61B protein (recombinantly expressed in *Aspergillus oryzae* as described herein) at 0.2, 0.4, 0.6 or 1.2 mg per g PCS and incubated for 115 hours. Results were compared with non-supplemented *Trichoderma reesei* broth at 2.5 and 3.5 mg per g PCS.

Figure 4:
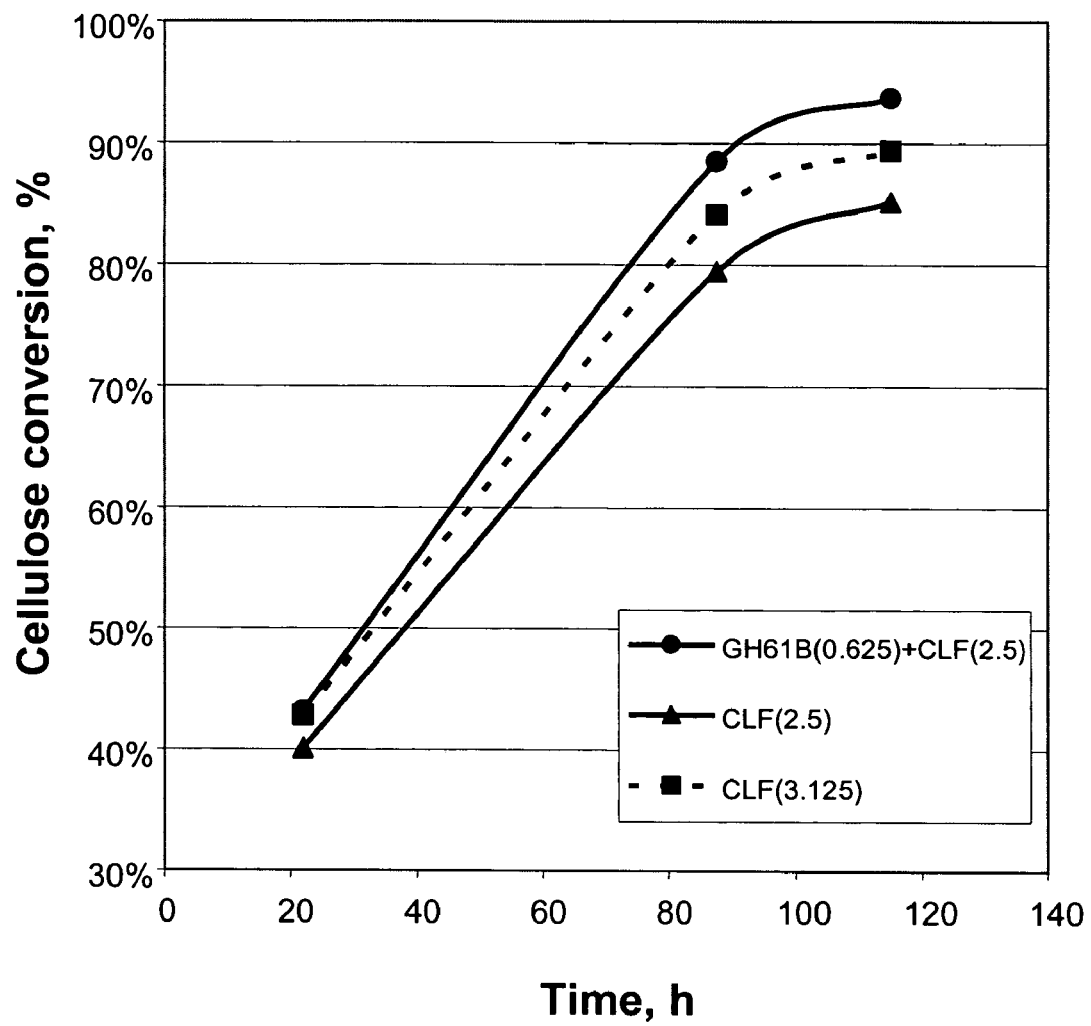
FIG. 4 shows the hydrolysis of PCS (P020502CS, 100 MF autoclaved, 10 g/L) by *Trichoderma reesei* broth expressing *Aspergillus oryzae* beta-glucosidase (CLF) with or without supplementation by *Trichoderma reesei* GH61B. Hydrolysis was carried out at 50° C., pH 5.0 for the indicated times. Celluclast Plus loading was 2.5 or 3.125 mg per gram of PCS and the mixture contained 2.5 mg of CLF and 0.625 mg of GH61B per gram of PCS.

Aliquots of 20 μl were removed from the PCS hydrolysis reactions at specified time points using an 8-channel pipettor, and added to 180 μl of an alkaline mixture (102 mM $Na_2CO_3$ and 58 mM $NaHCO_3$) in MultiScreen HV 96-well filtration plate (Millipore, Bedford, Mass.) to terminate the reaction. The samples were vacuum-filtered into another flat-bottomed microplate to remove the PCS residue. After appropriate dilution, the filtrates were analyzed for RS using the PHBAH assay described below The results as shown in FIG. 4 indicated that supplementing *Trichoderma reesei* fermentation broth expressing *Aspergillus oryzae* beta-glucosidase with the *Trichoderma reesei* GH61B protein improved the hydrolysis yield at all time points sampled. The improvement was greater than seen with an equal protein loading of the *Trichoderma reesei* broth alone. The improvement could not be explained by hydrolysis by the GH61B polypeptide alone as this amounted to only 1.2% at 115 hr even at a much higher protein loading of 2.5 mg per g of PCS.

Figure 5:
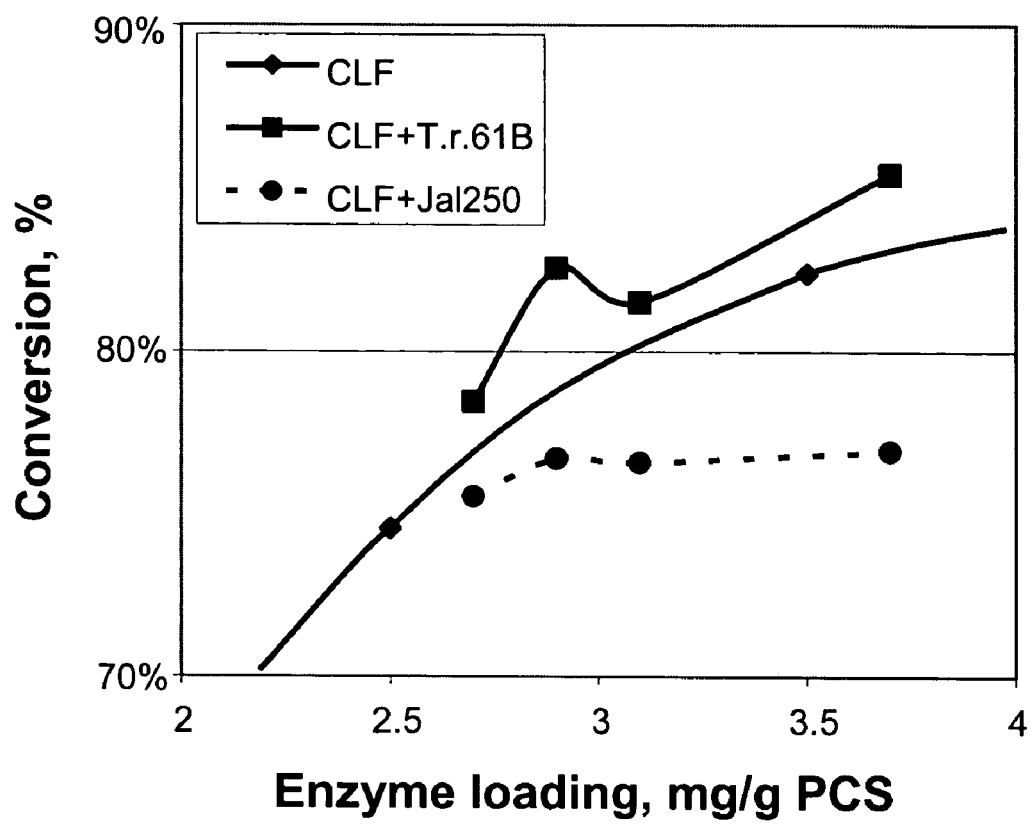
FIG. 5 the hydrolysis of PCS (P020502CS, 100 MF autoclaved, 10 g/L) by Celluclast Plus supplemented with GH61B protein. *Aspergillus oryzae* broth not containing recombinant protein (Jal250) was added as a control. Incubation was for 115 hours at 50° C.

The results shown in FIG. 5 indicated that the enhancement was seen over a range of protein loadings of the GH61B polypeptide, with maximal enhancement at a protein loading of approximately 16% of the protein loading of the *Trichoderma reesei* broth.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
|---|---|---|
| *E. coli* strain pTr3337 | NRRL B-30878 | Sep. 20, 2005 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for degrading or converting a cellulosic material, comprising: treating the cellulosic material with an effective amount of one or more cellulolytic proteins in the presence of an effective amount of a polypeptide having cellulolytic enhancing activity, wherein the presence of the polypeptide having cellulolytic enhancing activity increases the degradation of cellulosic material compared to the absence of the polypeptide having cellulolytic enhancing activity and wherein the polypeptide having cellulolytic enhancing activity does not itself degrade or convert the cellulosic material in the absence of one or more cellulolytic protein and wherein the polypeptide having cellulolytic enhancing activity is selected from the group consisting of:
  (a) a polypeptide comprising an amino acid sequence which has at least 95% sequence identity with the mature polypeptide of SEQ ID NO: 2;
  (b) a polypeptide encoded by a polynucleotide comprising a nucleotide sequence which has at least 95% sequence identity with the mature polypeptide coding sequence of SEQ ID NO: 1; and
  (c) a polypeptide encoded by a polynucleotide which hybridizes under at least high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii), wherein high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 65° C.

2. The method of claim 1, further comprising treating the cellulosic material with an effective amount of one or more enzymes selected from the group consisting of a hemicellulase, esterase, protease, laccase, peroxidase, or a mixture thereof.

3. The method of claim 1, further comprising recovering the degraded cellulosic material.

4. The method of claim 1, wherein the cellulolytic protein and/or the polypeptide having cellulolytic enhancing activity are in the form of a fermentation broth with or without cells.

5. The method of claim 1, wherein the polypeptide having cellulolytic enhancing activity comprises or consists of the amino acid, sequence of SEQ ID NO: 2 or the mature polypeptide thereof; or a fragment thereof having cellulolytic enhancing activity.

6. The method of claim 1, wherein the polypeptide having cellulolytic enhancing activity is encoded by the polynucleotide contained in plasmid pTr3337 which is contained in *E. coli* NRRL B-30878.

7. The method of claim 1, wherein the mature polypeptide coding sequence of SEQ ID NO: 1 is nucleotides 77 to 766 of SEQ ID NO: 1.

8. The method of claims 1, wherein the mature polypeptide of SEQ ID NO: 2 is amino acids 20 to 249 of SEQ ID NO: 2.

9. The method of claim 1, wherein the polypeptide having cellulolytic enhancing activity comprises an amino acid sequence which has at least 95% sequence identity with the mature polypeptide of SEQ ID NO: 2.

10. The method of claim 9, wherein the polypeptide having cellulolytic enhancing activity comprises an amino acid sequence which has at least 97% sequence identity with the mature polypeptide of SEQ ID NO: 2.

11. The method of claim 1, wherein the polypeptide having cellulolytic enhancing activity is encoded by a polynucleotide comprising a nucleotide sequence which has at least 95% a sequence identity with the mature polypeptide coding sequence of SEQ ID NO: 1.

12. The method of claim 11, wherein the polypeptide having cellulolytic enhancing activity is encoded by a polynucleotide comprising a nucleotide sequence which has at least 97% a sequence identity with the mature polypeptide coding sequence of SEQ ID NO: 1.

13. The method of claim 1, wherein the polypeptide having cellulolytic enhancing activity is encoded by a polynucleotide which hybridizes under high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii), wherein high stringency conditions are defined as prehybridization and hybridization at 42° C. in 5×SSPE, 0.30% SDS, 200 µg/ml sheared and denatured salmon sperm DNA and 50% a formamide and washing three times each for 15 minutes using 2×SSC, 0.2% SDS at 65° C.

* * * * *

SEQUENCE LISTING

<160> NUMBER OF SEQ ID NOS: 8

<210> SEQ ID NO 1
<211> LENGTH: 1172
<212> TYPE: DNA
<213> ORGANISM: Trichoderma reesei

<400> SEQUENCE: 1

```
ggatctaagc cccatcgata tgaagtcctg cgccattctt gcagcccttg gctgtcttgc      60
cgggagcgtt ctcggccatg gacaagtcca aaacttcacg atcaatggac aatacaatca     120
gggtttcatt ctcgattact actatcagaa gcagaatact ggtcacttcc ccaacgttgc     180
tggctggtac gccgaggacc tagacctggg cttcatctcc cctgaccaat acaccacgcc     240
cgacattgtc tgtcacaaga acgcggcccc aggtgccatt tctgccactg cagcggccgg     300
cagcaacatc gtcttccaat ggggcccggg cgtctggcct cacccctacg gtcccatcgt     360
tacctacgtg gctgagtgca gcggatcgtg cacgaccgtg aacaagaaca acctgcgctg     420
ggtcaagatt caggaggccg gcatcaacta taacacccaa gtctgggcgc agcaggatct     480
gatcaaccag ggcaacaagt ggactgtgaa gatcccgtcg agcctcaggc ccggaaacta     540
tgtcttccgc catgaacttc ttgctgccca tggtgcctct agtgcgaacg gcatgcagaa     600
ctatcctcag tgcgtgaaca tcgccgtcac aggctcgggc acgaaagcgc tccctgccgg     660
aactcctgca actcagctct acaagcccac tgaccctggc atcttgttca acccttacac     720
aacaatcacg agctacacca tccctggccc agccctgtgg caaggctaga tccaggggta     780
cggtgttggc gttcgtgaag tcggagctgt tgacaaggat atctgatgat gaacggagag     840
gactgatggg cgtgactgag tgtatatatt tttgatgacc aaattgtata cgaaatccga     900
acgcatggtg atcattgttt atccctgtag tatattgtct ccaggctgct aagagcccac     960
cgggtgtatt acggcaacaa agtcaggaat ttgggtggca atgaacgcag gtctccatga    1020
atgtatatgt gaagaggcat cggctggcat gggcattacc agatataggc cctgtgaaac    1080
atatagtact tgaacgtgct actggaacgg atcataagca agtcatcaac atgtgaaaaa    1140
acactacatg taaaaaaaaa aaaaaaaaaa aa                                  1172
```

```
<210> SEQ ID NO 2
<211> LENGTH: 249
<212> TYPE: PRT
<213> ORGANISM: Trichoderma reesei

<400> SEQUENCE: 2

Met Lys Ser Cys Ala Ile Leu Ala Ala Leu Gly Cys Leu Ala Gly Ser
1               5                   10                  15

Val Leu Gly His Gly Gln Val Gln Asn Phe Thr Ile Asn Gly Gln Tyr
            20                  25                  30

Asn Gln Gly Phe Ile Leu Asp Tyr Tyr Gln Lys Gln Asn Thr Gly
        35                  40                  45

His Phe Pro Asn Val Ala Gly Trp Tyr Ala Glu Asp Leu Asp Leu Gly
    50                  55                  60

Phe Ile Ser Pro Asp Gln Tyr Thr Thr Pro Asp Ile Val Cys His Lys
65                  70                  75                  80

Asn Ala Ala Pro Gly Ala Ile Ser Ala Thr Ala Ala Gly Ser Asn
                85                  90                  95

Ile Val Phe Gln Trp Gly Pro Gly Val Trp Pro His Pro Tyr Gly Pro
            100                 105                 110

Ile Val Thr Tyr Val Val Glu Cys Ser Gly Ser Cys Thr Thr Val Asn
        115                 120                 125

Lys Asn Asn Leu Arg Trp Val Lys Ile Gln Glu Ala Gly Ile Asn Tyr
    130                 135                 140

Asn Thr Gln Val Trp Ala Gln Gln Asp Leu Ile Asn Gln Gly Asn Lys
145                 150                 155                 160

Trp Thr Val Lys Ile Pro Ser Ser Leu Arg Pro Gly Asn Tyr Val Phe
                165                 170                 175

Arg His Glu Leu Leu Ala Ala His Gly Ala Ser Ser Ala Asn Gly Met
            180                 185                 190

Gln Asn Tyr Pro Gln Cys Val Asn Ile Ala Val Thr Gly Ser Gly Thr
        195                 200                 205

Lys Ala Leu Pro Ala Gly Thr Pro Ala Thr Gln Leu Tyr Lys Pro Thr
    210                 215                 220

Asp Pro Gly Ile Leu Phe Asn Pro Tyr Thr Thr Ile Thr Ser Tyr Thr
225                 230                 235                 240

Ile Pro Gly Pro Ala Leu Trp Gln Gly
                245

<210> SEQ ID NO 3
<211> LENGTH: 25
<212> TYPE: DNA
<213> ORGANISM: Trichoderma reesei
<220> FEATURE:
<221> NAME/KEY: misc_feature
<222> LOCATION: (24)..(24)
<223> OTHER INFORMATION: V= G, A, OR C
<220> FEATURE:
<221> NAME/KEY: misc_feature
<222> LOCATION: (25)..(25)
<223> OTHER INFORMATION: N= A, C, G, OR T

<400> SEQUENCE: 3
tttttttttt tttttttttt tttvn                                    25

<210> SEQ ID NO 4
<211> LENGTH: 15
<212> TYPE: DNA
```

```
<213> ORGANISM: Trichoderma reesei

<400> SEQUENCE: 4
tgtccatggc cgaga                                                   15

<210> SEQ ID NO 5
<211> LENGTH: 19
<212> TYPE: DNA
<213> ORGANISM: Trichoderma reesei

<400> SEQUENCE: 5
atactggtca cttccccaa                                               19

<210> SEQ ID NO 6
<211> LENGTH: 16
<212> TYPE: DNA
<213> ORGANISM: Trichoderma reesei

<400> SEQUENCE: 6
gcgctgggtc aagatt                                                  16

<210> SEQ ID NO 7
<211> LENGTH: 35
<212> TYPE: DNA
<213> ORGANISM: Trichoderma reesei

<400> SEQUENCE: 7
actggattta ccatgaagtc ctgcgccatt cttgc                             35

<210> SEQ ID NO 8
<211> LENGTH: 33
<212> TYPE: DNA
<213> ORGANISM: Trichoderma reesei

<400> SEQUENCE: 8
agtcacctct agttagccttt gccacagggc tgg                              33
```